US012654409B2

(12) United States Patent (10) Patent No.: US 12,654,409 B2
Chalberg, Jr. et al. (45) Date of Patent: Jun. 16, 2026

(54) OPHTHALMIC LENSES, METHODS OF MANUFACTURING THE OPHTHALMIC LENSES, AND METHODS OF DISPENSING EYE CARE PRODUCTS INCLUDING THE SAME

(71) Applicant: SIGHTGLASS VISION, INC., Palo Alto, CA (US)

(72) Inventors: Thomas W. Chalberg, Jr., Menlo Park, CA (US); Peter Hones, Menlo Park, CA (US); Axel Leroy Smith, Sunnyvale, CA (US)

(73) Assignee: SightGlass Vision, Inc., Dallas, TX (US)

( * ) Notice: Subject to any disclaimer, the term of this patent is extended or adjusted under 35 U.S.C. 154(b) by 440 days.

(21) Appl. No.: 17/926,442

(22) PCT Filed: May 18, 2021

(86) PCT No.: PCT/US2021/033026
§ 371 (c)(1),
(2) Date: Nov. 18, 2022

(87) PCT Pub. No.: WO2021/236687
PCT Pub. Date: Nov. 25, 2021

(65) Prior Publication Data
US 2023/0181030 A1    Jun. 15, 2023

Related U.S. Application Data

(60) Provisional application No. 63/062,687, filed on Aug. 7, 2020, provisional application No. 63/027,229, filed on May 19, 2020.

(51) Int. Cl.
*B29D 11/00* (2006.01)
*A61B 3/10* (2006.01)
*A61F 2/16* (2006.01)

(52) U.S. Cl.
CPC ...... B29D 11/00009 (2013.01); A61B 3/1015 (2013.01); A61F 2/16 (2013.01)

(58) Field of Classification Search
CPC ...... G02C 2202/24; G02C 7/022; G02C 7/06; G02C 7/086; G02C 7/061; G02C 7/021;
(Continued)

(56) References Cited

U.S. PATENT DOCUMENTS 5,963,298 A  *  10/1999  Bard ...................... G02C 7/046
                                               351/159.28
6,997,554 B2     2/2006  Nakada et al.
(Continued)

FOREIGN PATENT DOCUMENTS

AU        2009237561 A1    10/2009
CN          1980771 A       6/2007
(Continued)

OTHER PUBLICATIONS

Office Action in Singaporean Appln. No. 11202260349V, dated Jun. 11, 2024, 10 pages.
(Continued)

*Primary Examiner* — Matthew Y Lee
(74) *Attorney, Agent, or Firm* — Fish & Richardson P.C.

(57)                    ABSTRACT

Ophthalmic lenses and method of manufacturing ophthalmic lenses are disclosed. The lenses are manufactured with markers for aligning the lenses in a particular rotational alignment with respect to a spectacle frame. The lenses can also be provided with scattering parts for defocus to prevent myopia.

25 Claims, 22 Drawing Sheets

(58) Field of Classification Search

CPC ...... G02C 2202/20; G02C 7/02; G02C 7/105; B29D 11/00326; B29L 2011/00; G02B 3/10; G02B 3/02

See application file for complete search history.

(56) References Cited

U.S. PATENT DOCUMENTS

| | | | |
|---|---|---|---|
| 7,506,983 | B2 | 3/2009 | To et al. |
| 7,901,075 | B2 | 3/2011 | Rooney et al. |
| 8,115,792 | B2 | 2/2012 | Petsch et al. |
| 10,126,566 | B2 | 11/2018 | Mizuno et al. |
| 10,203,522 | B2 | 2/2019 | Bakaraju et al. |
| 10,268,050 | B2 | 4/2019 | To et al. |
| 10,429,670 | B2 | 10/2019 | Newman |
| 10,517,717 | B2 | 12/2019 | Inoue |
| 2005/0104240 | A1 | 5/2005 | Jethmalani et al. |
| 2005/0105043 | A1 | 5/2005 | Dreher et al. |
| 2005/0206840 | A1 | 9/2005 | Roscini |
| 2007/0177101 | A1 | 8/2007 | Divo |
| 2010/0157242 | A1 | 6/2010 | Esser et al. |
| 2010/0222517 | A1 | 9/2010 | Hino et al. |
| 2011/0313058 | A1 | 12/2011 | Neitz et al. |
| 2017/0146824 | A1 | 5/2017 | Martinez et al. |
| 2017/0299886 | A1* | 10/2017 | Carmon ................. B41J 3/4073 |
| 2018/0017810 | A1 | 1/2018 | Wu |
| 2018/0275427 | A1* | 9/2018 | Lau ........................ G02C 7/081 |
| 2018/0307058 | A1 | 10/2018 | Welscher et al. |
| 2019/0033619 | A1* | 1/2019 | Neitz ....................... G02C 7/16 |
| 2019/0219840 | A1* | 7/2019 | Keane .................... G02C 7/027 |
| 2019/0235279 | A1* | 8/2019 | Hones .................... G02C 7/021 |
| 2020/0073147 | A1 | 3/2020 | Bakaraju et al. |
| 2020/0089023 | A1 | 3/2020 | Zhou et al. |
| 2021/0282966 | A1* | 9/2021 | Back ...................... G02C 7/027 |
| 2022/0011594 | A1* | 1/2022 | Newman ................ G02C 7/022 |
| 2023/0101527 | A1* | 3/2023 | Bakaraju .................. G02B 3/02 351/159.42 |
| 2023/0229018 | A1* | 7/2023 | Qi .......................... G02C 7/022 351/159.79 |
| 2023/0314840 | A1* | 10/2023 | Zhou ........................ G02C 7/06 351/159.46 |

FOREIGN PATENT DOCUMENTS

| | | |
|---|---|---|
| CN | 201804169 | 4/2011 |
| CN | 109031696 | 12/2018 |
| CN | 109581690 | 4/2019 |
| CN | 110068938 | 7/2019 |
| CN | 116157709 A | 5/2023 |
| EP | 2962155 | 1/2016 |
| EP | 3300694 A1 | 4/2018 |
| EP | 3647859 | 5/2020 |
| EP | 3667401 | 6/2020 |
| FR | 2819897 | 7/2002 |
| JP | 2005-324316 A | 11/2005 |
| JP | 2007-025322 | 2/2007 |
| JP | 2019-529968 | 10/2019 |
| JP | 2023526484 A | 6/2023 |
| KR | 100840845 | 6/2008 |
| KR | 10-1863313 | 5/2018 |
| TW | 200912425 A | 3/2009 |
| TW | 201329557 A | 7/2013 |
| TW | 201702692 | 1/2017 |
| WO | WO 2003/035377 | 5/2003 |
| WO | WO 2008/089995 | 7/2008 |
| WO | WO 2009/038142 | 3/2009 |
| WO | WO 2010/075319 | 7/2010 |
| WO | WO 2012/097213 | 7/2012 |
| WO | WO 2013/113798 | 8/2013 |
| WO | WO 2016/138512 | 9/2016 |
| WO | WO 2018/026697 | 2/2018 |
| WO | WO 2018/208724 | 11/2018 |
| WO | WO 2019/152438 | 8/2019 |
| WO | WO 2019/166653 | 9/2019 |
| WO | WO 2019/166654 | 9/2019 |
| WO | WO 2019/166655 | 9/2019 |
| WO | WO 2019/166657 | 9/2019 |
| WO | WO 2019/166659 | 9/2019 |
| WO | WO 2019/206569 | 10/2019 |
| WO | WO 2020/014613 | 1/2020 |
| WO | WO 2020/069232 | 4/2020 |
| WO | WO 2020/113212 | 6/2020 |
| WO | WO 2020/138127 | 7/2020 |
| WO | WO 2020/180817 | 9/2020 |
| WO | WO 2020/219518 | 10/2020 |
| WO | WO 2021/236687 A3 | 11/2021 |

OTHER PUBLICATIONS

Office Action in Korean Appln. No. 10-2022-7044080, dated Nov. 18, 2024, 28 pages (with English translation).

Office Action in Japanese Appln. No. 2022-570705, dated Nov. 6, 2023, 14 pages (with English translation).

International Preliminary Report on Patentability in International Appln. No. PCT/US2021/033026, mailed on Dec. 1, 2022, 16 pages.

International Search Report and Written Opinion in International Appln. No. PCT/US2021/033026, mailed on Dec. 3, 2021, 27 pages.

Invitation to Pay Additional Fees and, Where Applicable, Protest Fee in International Appln. No. PCT/US2021/033026, mailed on Sep. 3, 2021, 11 pages.

Office Action in Taiwanese Appln. No. 110118122, dated Dec. 9, 2022, 37 pages (with English translation).

Sankaridurg et al., "Spectacle Lenses Designed to Reduce Progression of Myopia: 12-Month Results," Optom. Vis Sci., Sep. 2010, 87(9):631-641.

Shaw, "Optical System Design—S15," Montana State University, Aug. 4, 2016, retrieved on Sep. 1, 2023, retrieved from <https://www.montana.edu/jshaw/documents/18%20EELE582_S15_OTFMTF.pdf>, 18 pages.

Yeo et al. "Myopia and Effective Management Solutions," Points de Vue—International Review of Ophthalmic Optics, Autumn 2016, 73:56-65.

Office Action in Chinese Appln. No. 202180060043.7, Mar. 29, 2025, 17 pages (with English translation).

Office Action in Australian Appln. No. 2024216341, mailed on Sep. 15, 2025, 5 pages.

Office Action in Chinese Appln. No. 202180060043.7, dated Mar. 4, 2026, 19 pages (with Machine Translation).

Office Action in Japanese Appln. No. 2025-092703, dated Apr. 28, 2026, 14 pages (with Machine Translation).

* cited by examiner

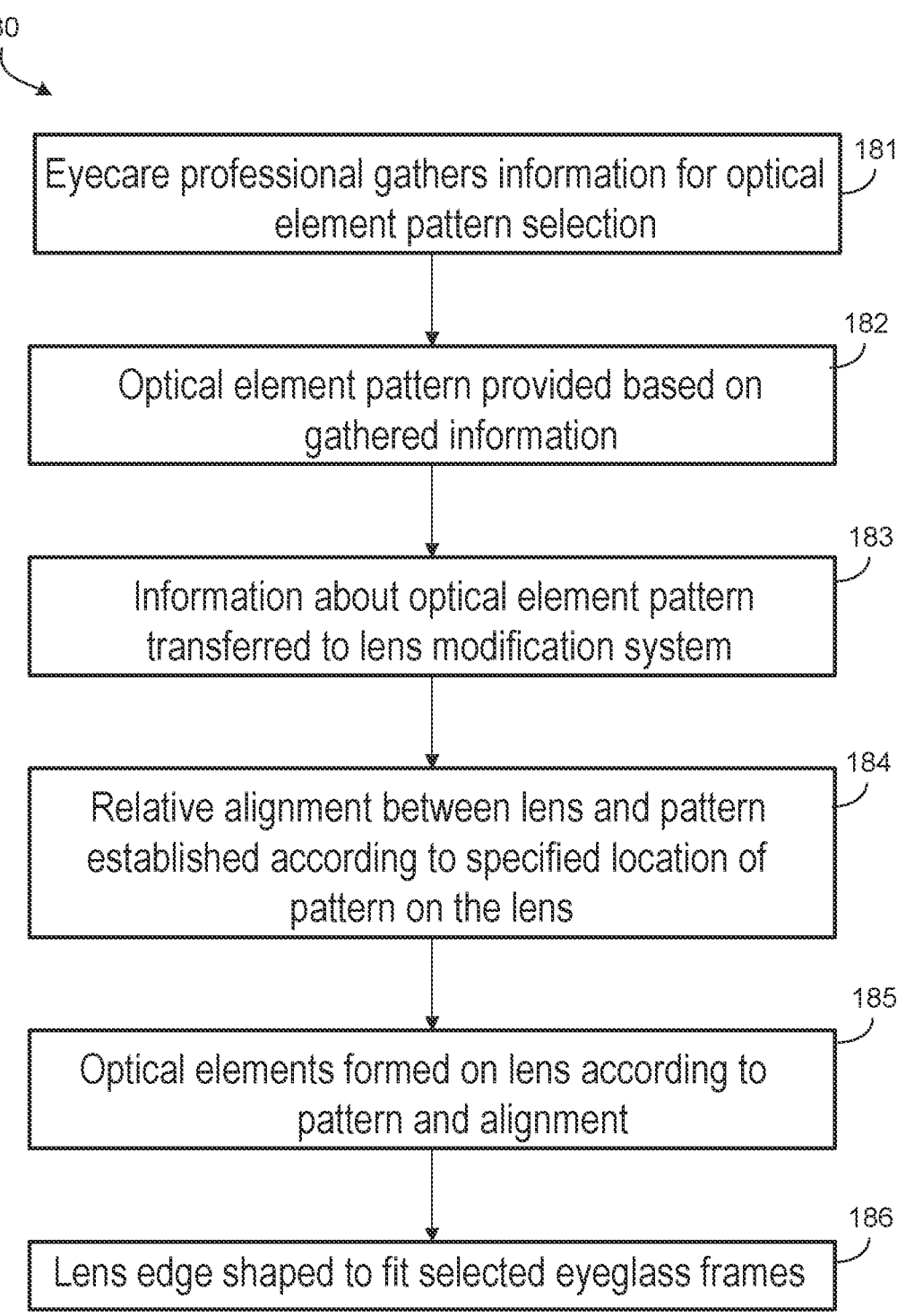

180

181
Eyecare professional gathers information for optical element pattern selection 182
Optical element pattern provided based on gathered information 183
Information about optical element pattern transferred to lens modification system 184
Relative alignment between lens and pattern established according to specified location of pattern on the lens 185
Optical elements formed on lens according to pattern and alignment 186
Lens edge shaped to fit selected eyeglass frames

FIG. 1B

SPH= 0.00D
CYL= 0.00D

SPH= -1.00D
CYL= 0.00D

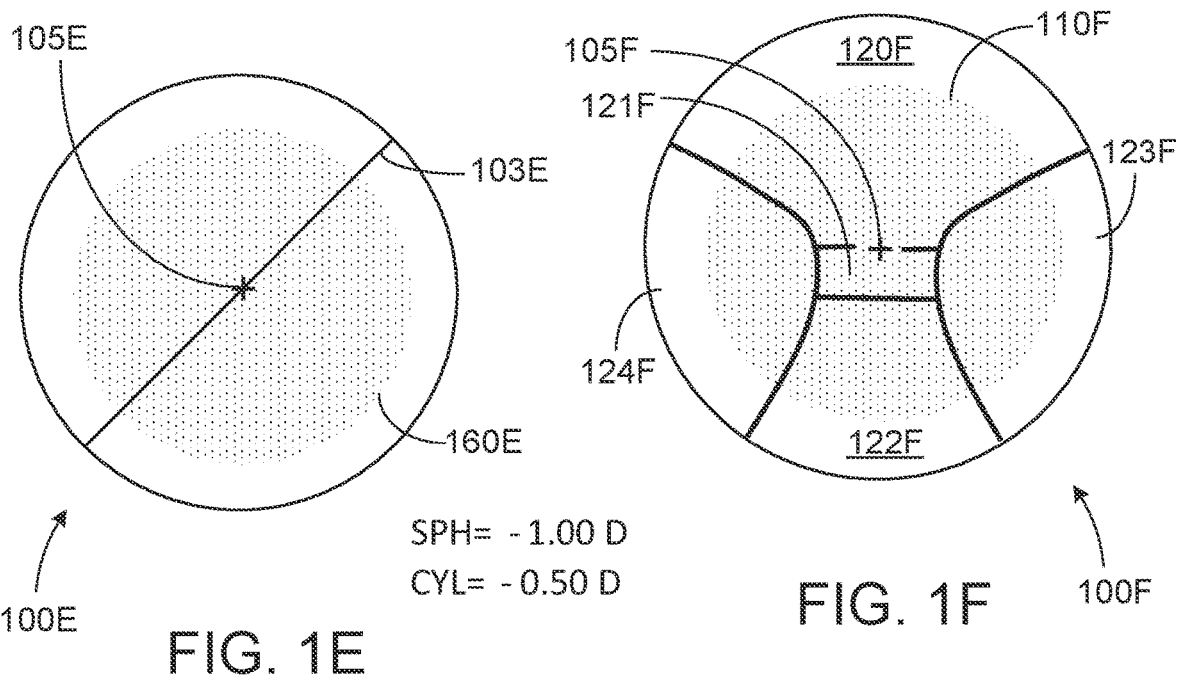
SPH= -1.00 D
CYL= -0.50 D
FIG. 1E
FIG. 1F
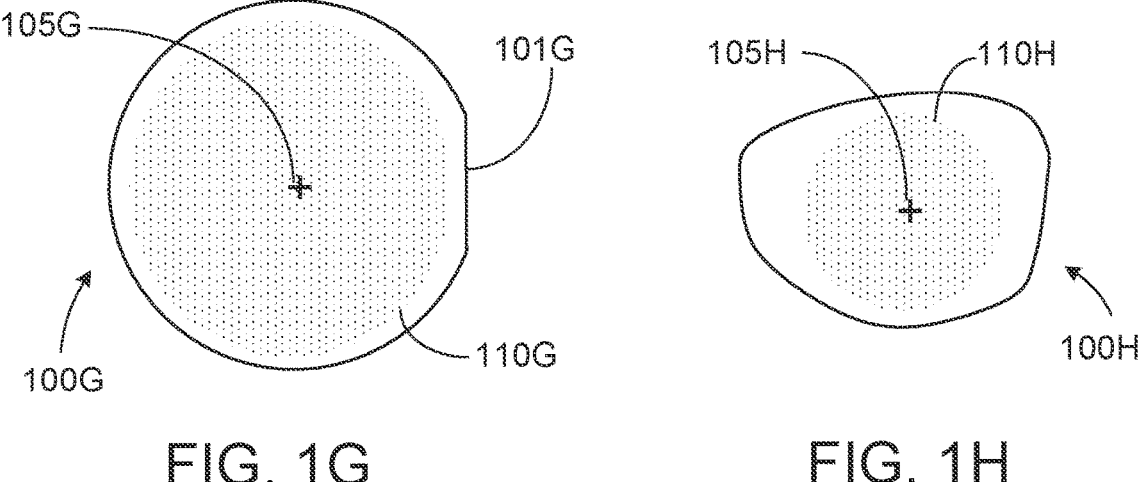
FIG. 1G
FIG. 1H

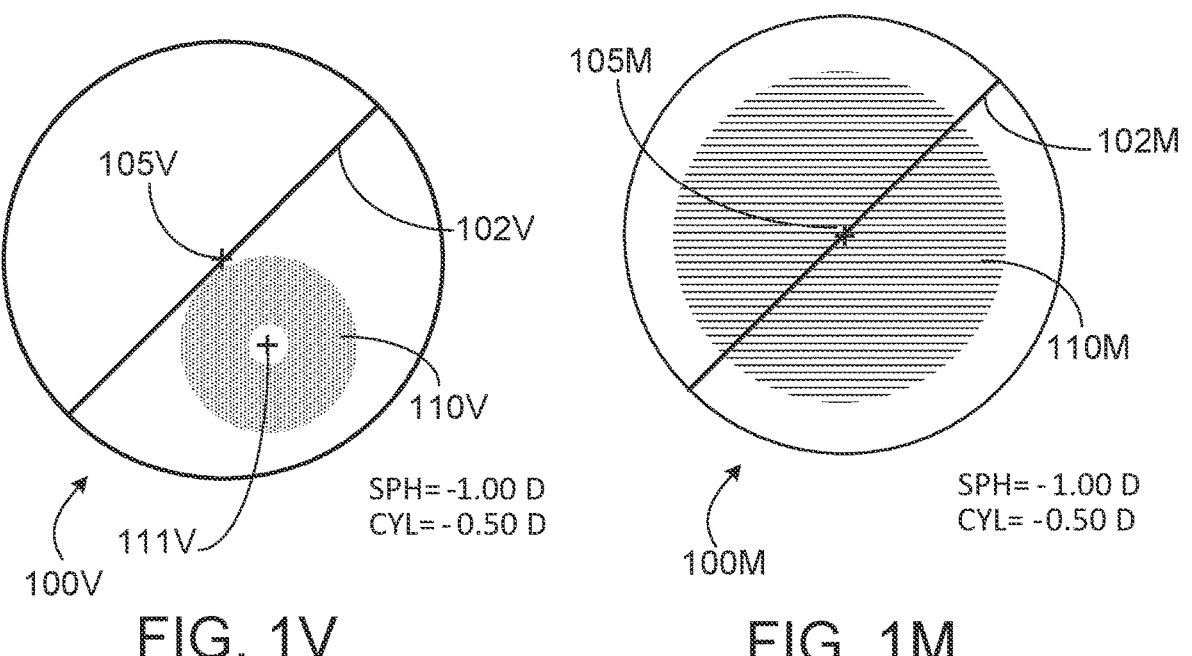
SPH= -1.00 D
CYL= -0.50 D
FIG. 1V
SPH= -1.00 D
CYL= -0.50 D
FIG. 1M
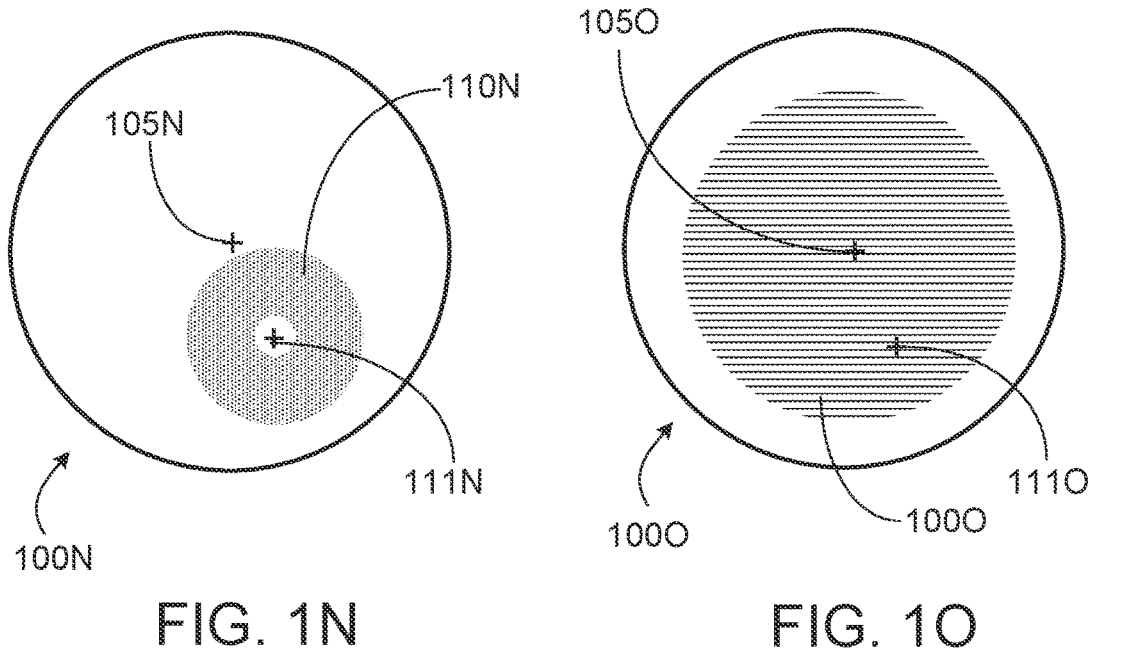
FIG. 1N
FIG. 1O

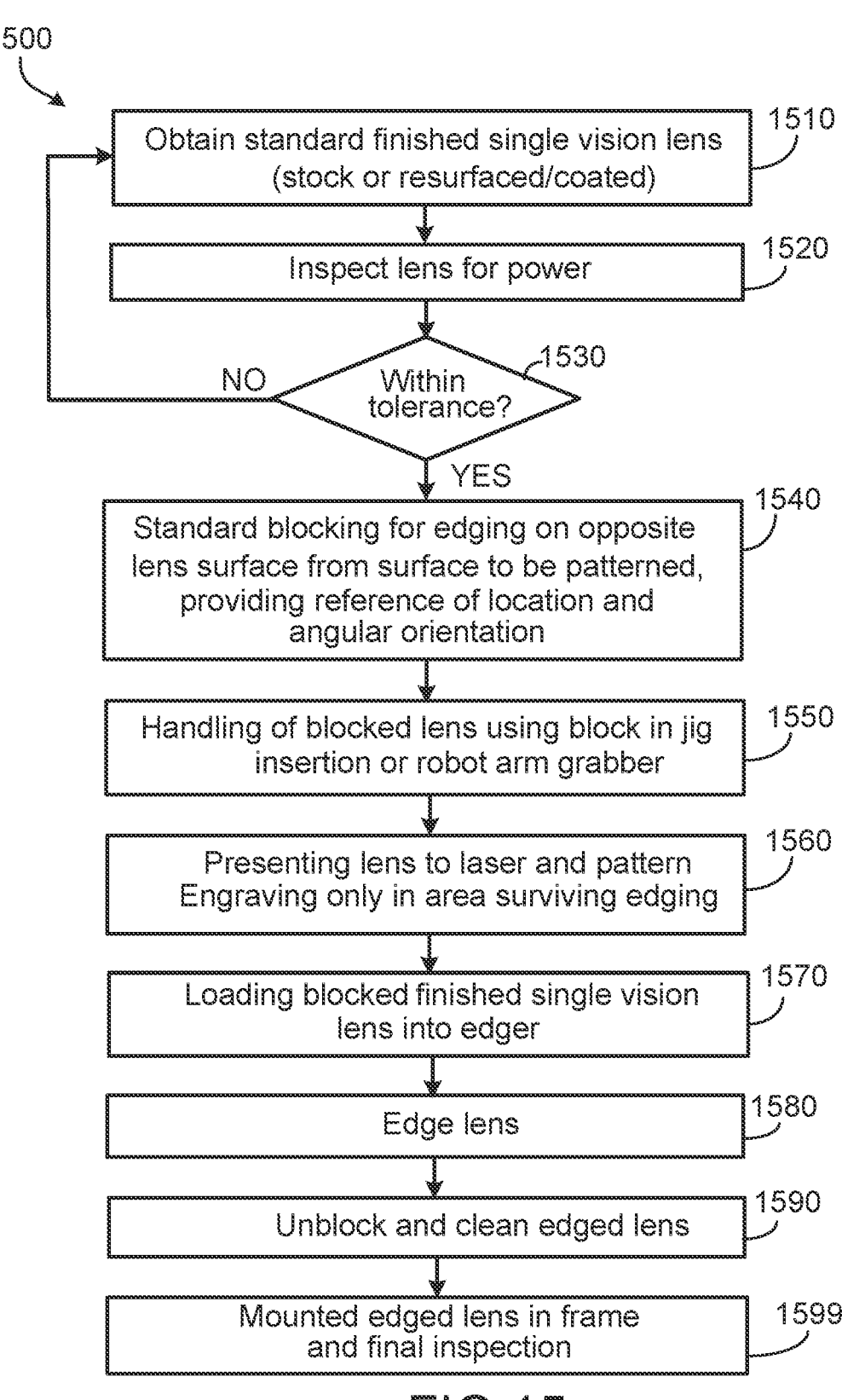

1500

1510 Obtain standard finished single vision lens (stock or resurfaced/coated)

1520 Inspect lens for power

1530 Within tolerance?

NO

YES

1540 Standard blocking for edging on opposite lens surface from surface to be patterned, providing reference of location and angular orientation 1550 Handling of blocked lens using block in jig insertion or robot arm grabber 1560 Presenting lens to laser and pattern Engraving only in area surviving edging 1570 Loading blocked finished single vision lens into edger 1580 Edge lens 1590 Unblock and clean edged lens 1599 Mounted edged lens in frame and final inspection

FIG.15

OPHTHALMIC LENSES, METHODS OF MANUFACTURING THE OPHTHALMIC LENSES, AND METHODS OF DISPENSING EYE CARE PRODUCTS INCLUDING THE SAME

CROSS-REFERENCE TO RELATED APPLICATIONS

This application claims priority to U.S. Patent Application No. 63/027,229, filed May 19, 2020, and to U.S. Patent Application No. 63/062,687, filed Aug. 7, 2020. The entirety of each of the foregoing is hereby incorporated by reference.

FIELD OF THE DISCLOSURE

This disclosure relates to ophthalmic lenses and to methods of making ophthalmic lenses. More particularly, this disclosure relates, at least in part, to Just-In-Time manufacturing of ophthalmic lenses. In some embodiments this disclosure relates to Just-In-Time manufacturing of ophthalmic lenses that can be used to reduce myopia progression in a user.

BACKGROUND

The eye is an optical sensor in which light from external sources is focused, by a lens, onto the surface of the retina, an array of wavelength-dependent photosensors. The lens of the eye can accommodate by changing shape such that the focal length at which external light rays are optimally or near-optimally focused to produce inverted images on the surface of the retina that correspond to external images observed by the eye. The eye lens focuses light, optimally or near-optimally, emitted by, or reflected from external objects that lie within a certain range of distances from the eye, and less optimally focuses, or fails to focus objects that lie outside that range of distances.

In normal-sighted individuals, the axial length of the eye, or distance from the front of the cornea to the fovea of the retina, corresponds to a focal length for near-optimal focusing of distant objects. The eyes of normal-sighted individuals focus distant objects without nervous input to muscles which apply forces to alter the shape of the eye lens, a process referred to as "accommodation." Closer, nearby objects are focused, by normal individuals, as a result of accommodation.

Many people, however, suffer from eye-length-related disorders, such as myopia ("nearsightedness"). In myopic individuals, the axial length of the eye is longer than the axial length required to focus distant objects without accommodation. As a result, myopic individuals can view near objects at a certain distance clearly, but objects further away from that distance are blurry.

Typically, infants are born hyperopic, with eye lengths shorter than needed for optimal or near-optimal focusing of distant objects without accommodation. During normal development of the eye, referred to as "emmetropization," the axial length of the eye, relative to other dimensions of the eye, increases up to a length that provides near-optimal focusing of distant objects without accommodation. Ideally, biological processes maintain the near-optimal relative eye length to eye size (e.g., axial length) as the eye grows to final, adult size. However, in myopic individuals, the relative axial length of the eye to overall eye size continues to increase during development, past a length that provides near-optimal focusing of distant objects, leading to increasingly pronounced myopia.

It is believed that myopia is affected by environmental factors as well as genetic factors. Accordingly, myopia may be mitigated by therapeutic devices which address environmental factors. For example, therapeutic devices for treating eye-length related disorders, including myopia, are described in U.S. Pub. No. 2011/0313058A1.

Therapeutic devices for reducing myopic progression include certain ophthalmic lenses, such as certain eyeglass lenses and certain contact lenses. Prescription eyeglasses and contact lenses are commonly dispensed through eye care professional offices or via online dispensaries. In each case, particularly for eyeglasses, these devices are customized specifically for each patient. For example, a patient can select a pair of eyeglasses from a substantial range of styles and brands. For a given prescription, they can also select from a variety of different stock lenses with a variety of different possible coatings (e.g., hardcoats and optical filters, such as short-wavelength filters, and/or photochromic filters). Multi-focal lenses are also possible, which involve an even higher degree of customization. In each case, the eyeglasses are provided to their end user in a timely fashion by virtue of a supply chain than enables Just-In-Time manufacturing the eyeglasses. Lens manufacturers generally supply stock lenses to regional supply centers that can customize the lenses to, e.g., shape one or both lens surfaces, apply coatings to one or both of the lens surfaces, and shape what are usually circular blanks to fit specific eyeglass frames selected by the user. The latter process generally takes into consideration the specific interpupillary distance of the patient and optical center heights with respect to the vertical pupil locations relative to the specific eyeglass frame.

SUMMARY

Certain manufacturing methods for forming patterns of optical element on a stock ophthalmic lens can be performed economically at or close to the point-of-sale of eyeglasses to their end user. For example, certain manufacturing methods can be deployed at an eye care professional's office, or at a regional lens distributor. Moreover, some of these manufacturing methods allow for a high degree of customization of the pattern of the optical elements on an ophthalmic lens, which can be either a stock ophthalmic lens such as a finished single vision lens (i.e., a plano lens, a spherical lens, a cylinder lens, or a toric lens), or a surfaced ophthalmic lens, such as a digitally surfaced single vision lens, a multifocal lens, a progressive lens, and the like. Accordingly, these methods can be used to provide a high degree of customization of optical element patterns on a variety of different stock or surfaced ophthalmic lenses, in much the same way that various lens coatings are provided. These methods can be referred to as Just-In-Time (JIT) delivery methods, facilitating rapid delivery of a customized product to the user. Moreover, these methods can be readily deployed within existing supply chains for prescription eyeglass delivery to consumers.

In general, in a first aspect, the invention features a method that includes providing an ophthalmic lens having opposing surfaces defining an optical power of the ophthalmic lens (e.g., with one or both surfaces finished), one or both of the opposing surfaces further defining an optical center of the ophthalmic lens, and the ophthalmic lens including an edge defining a perimeter of the ophthalmic lens; obtaining a pattern of three or more optical elements; and forming the optical elements on the lens according to the pattern. The at least three optical elements each have an optical effect different from the optical power of the ophthalmic lens. (i) The pattern is radially asymmetric, or (ii) the ophthalmic lens has at least one optical or structural characteristic (e.g., a marker or feature in the edge of the lens) that is radially asymmetric with respect to the ophthalmic lens; and (i) the ophthalmic lens is radially asymmetric and the pattern is formed on the ophthalmic lens according to a specified orientation, or (ii) one or more optical or structural features are formed on at least one surface and/or edge of the ophthalmic lens that specifies a rotational orientation of the ophthalmic lens.

In general, in another aspect, the invention features a method that includes receiving an ophthalmic lens having opposing surfaces defining an optical power of the ophthalmic lens, one or both of the opposing surfaces further defining an optical center of the ophthalmic lens, and the ophthalmic lens having an edge defining a perimeter of the ophthalmic lens, the ophthalmic lens being optically and structurally radially symmetric about the optical axis; obtaining a pattern of three or more optical elements, wherein the pattern is radially asymmetric; forming the optical elements on the lens according to the pattern; forming one or more structural features on at least one surface and/or edge of the ophthalmic lens that can be used to specify the rotational orientation of the lens, wherein the at least three optical elements each have an optical effect different from the optical power of the ophthalmic lens.

In general, in another aspect, the invention features a method that includes providing an ophthalmic lens having opposing surfaces defining an optical power of the ophthalmic lens, one or both of the opposing surfaces further defining an optical center of the ophthalmic lens, and the ophthalmic lens comprising an edge defining a perimeter of the ophthalmic lens, the ophthalmic lens having at least one optical or structural characteristic that is radially asymmetric about the optical axis; obtaining a pattern of three or more optical elements, wherein the pattern is radially asymmetric about its center; specifying, using a data processing apparatus, a relative orientation of the ophthalmic lens and the pattern; and forming the optical elements on the lens according to the pattern and the specified orientation, wherein the at least three optical elements each have an optical effect different from the optical power of the ophthalmic lens.

In general, in yet another aspect, the invention features a method that includes receiving an ophthalmic lens having opposing surfaces defining an optical power of the ophthalmic lens, one or both of the opposing surfaces further defining an optical center of the ophthalmic lens, and the ophthalmic lens having an edge defining a perimeter of the ophthalmic lens, the ophthalmic lens being radially symmetric about the optical axis; obtaining a pattern of three or more optical elements, wherein the pattern is radially asymmetric; forming the optical elements on the lens according to the pattern; forming one or more optical or structural features on at least one surface and/or edge of the ophthalmic lens that specifies a rotational orientation of the lens with respect to an axis passing through a geometric center of the lens, wherein the at least three optical elements each have an optical effect different from the optical power of the ophthalmic lens.

In a further aspect, the invention features an article that includes an ophthalmic lens having opposing surfaces defining an optical power of the ophthalmic lens, one or both of the opposing surfaces further defining an optical center of the ophthalmic lens, and the ophthalmic lens includes an edge defining a perimeter of the ophthalmic lens, the ophthalmic lens having at least one optical or structural characteristic that is not radially symmetric about the optical center; a pattern of three or more optical elements having an outline and/or a density distribution defining an image viewable from a world side of spectacles containing the ophthalmic lens, wherein the image is not radially symmetric about the optical center. In another aspect, the invention features a method that includes receiving, at a data processing apparatus, user-specified input parameter values; determining, using the data processing apparatus and based on the input parameter values, a pattern of optical elements for forming on a surface of an ophthalmic lens; and providing, on a surface of the ophthalmic lens, optical elements according to the pattern.

In yet a further aspect, the invention features a method for forming an ophthalmic lens for reducing myopic progression in a human patient, including: receiving, at a data processing apparatus, information characterizing the ophthalmic lens based on a refractive error of the human patient; determining, by the data processing apparatus, a pattern of optical elements for forming on a surface of the ophthalmic lens, the pattern of optical elements being selected for reducing myopic progression of the human patient; and making the ophthalmic lens based on the information and the pattern of optical elements, wherein a surface of the ophthalmic lens includes one or more portions having a base curvature corresponding to an optical power for correcting the refractive error of the human patient and the pattern of optical elements.

In still a further aspect, the invention features a system for forming an ophthalmic lens for reducing myopic progression in a human patient from a stock ophthalmic lens selected for the human patient, the system including: an input terminal for receiving information about the stock ophthalmic lens and information about the human patient; a data processing apparatus programmed to receive the information about the stock ophthalmic lens and the information about the human patient from the input terminal and to output a pattern of optical elements for forming on a surface of the stock ophthalmic lens, the pattern of optical elements being selected to reduce myopic progression of the human patient; and a lens surface modification apparatus arranged to receive the pattern of optical elements output by the data processing apparatus and to form optical elements on a surface of the ophthalmic lens according to the pattern.

Each of the aforementioned aspects can include one or more features enumerated in the claims and/or described in the description below.

BRIEF DESCRIPTION OF THE DRAWINGS

FIG. 1B is a flowchart showing an example method for making an ophthalmic lens that includes optical elements.

FIGS. 1E-1H are plan view diagrams showing are examples of radially asymmetric ophthalmic lenses with radially symmetric patterns.

FIGS. 1M-1V are plan view diagrams showing examples of ophthalmic lenses

FIG. 4 is a plan view of an example tray for supporting ophthalmic lenses during a manufacturing process.

FIG. 15 is a flow chart showing steps in an example ophthalmic lens manufacturing method.

DETAILED DESCRIPTION

Figure 1A:
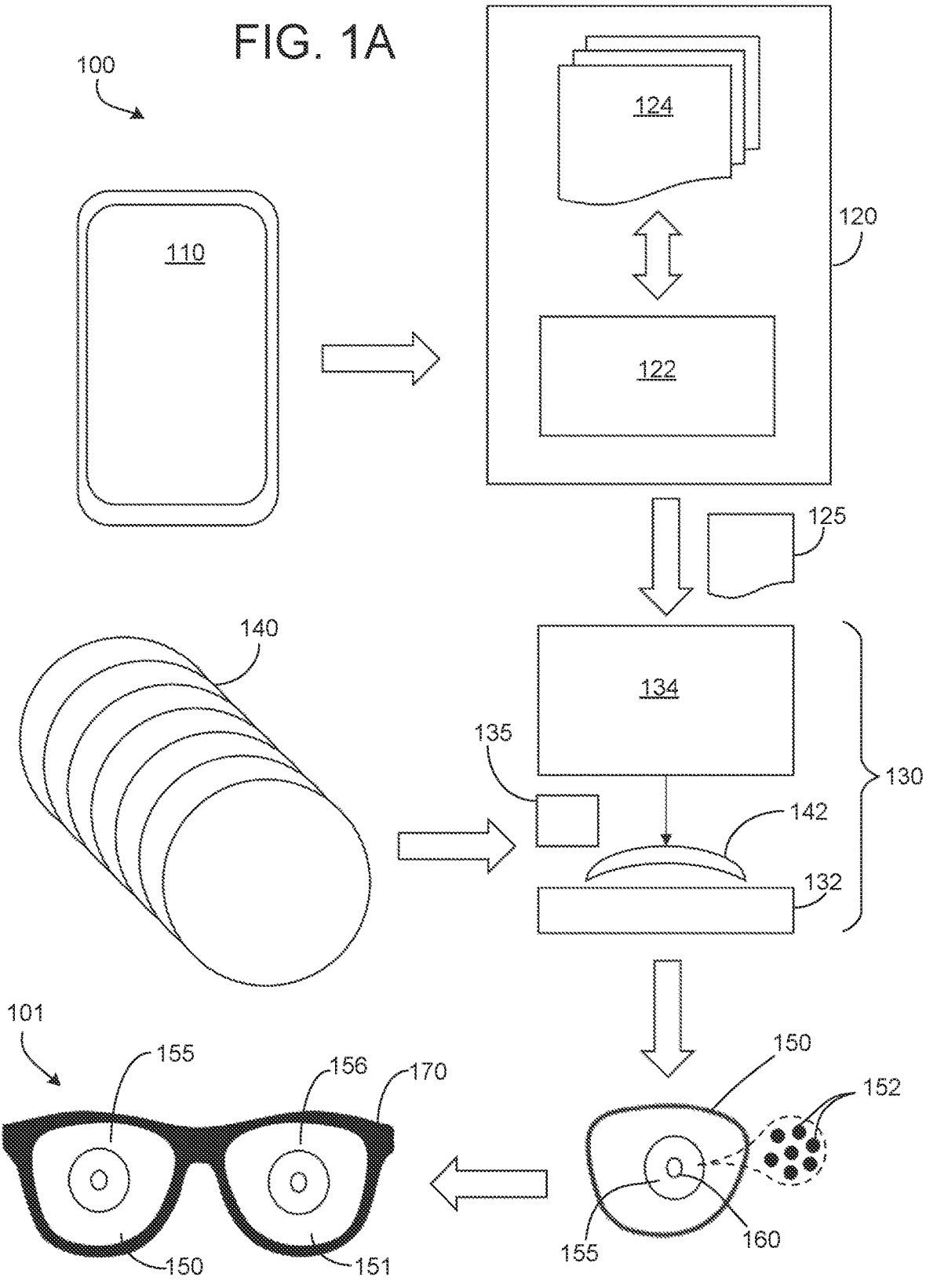
FIG. 1A is a diagram illustrating an example system and workflow for delivering customized ophthalmic lenses for a pair of eyeglasses.

Referring to FIG. 1A, an example system 100 for dispensing eyeglasses 101 includes an input terminal 110 and a data processing apparatus 120 in communication with a lens modification system 130. Eyeglasses 101 include lenses 150 and 151 that are mounted in eyeglass frames 170. Each lens 150, 151 includes a pattern 155, 156 of optical elements that are formed on the lenses by lens modification system 130 as part of a customization process.

Input terminal 110 can be, for example, a computer terminal or a mobile device (such as tablet computer or mobile phone) running a software application facilitating operation of system 100. Data processing apparatus 120 includes a processing module 122 (e.g., with one or more computer processors), which retrieves or calculates information 124 about pattern 155 of optical elements to be formed on the lens. For example, the optical elements can include lenslets, scattering centers, and/or Fresnel lens elements, which can be arranged according to pattern 155. In some embodiments, the optical elements reduce progression of myopia in the user of eyeglasses 101. Upon selection, system 100 sends information 125 about pattern 155 to lens modification system 130.

System 100 is designed to allow modification of a variety of lenses 140 to include pattern 155 of optical elements. That is, the system is designed to modify lens blanks available commercially from numerous ophthalmic lens companies. These include single vision prescription lenses, multifocal lenses, and plano lenses. The lenses 140 are generally formed from glass or a plastic. A lens 142 for modification is typically selected according to the needs (e.g., Rx) and preferences (e.g., lens material, coatings) of the user.

Lens modification system 130 includes a platform 132 which positions the selected lens 142 relative to an exposure apparatus 134 or vice versa. Depending on the implementation, the exposure apparatus 134 can either deposit material on a surface of the lens to form the optical elements, or it exposes the lens to radiation which modifies the surface and/or bulk of lens 142 to form the optical elements. Lens modification system 130 also includes a lens alignment module, e.g., an optical alignment module or a physical stop, which aligns lens 142 relative to exposure apparatus 134 to ensure that the pattern is formed according to a specified relative alignment between the lens and the pattern.

System 100 controls the relative orientation between lens 142 and exposure apparatus 134 to form optical elements on the lens according to the pattern 155. After forming pattern 155 of optical elements 152 on lens 142, the edge of the lens is shaped (e.g., milled) to fit eyeglass frames 170 in a process commonly called edging. Alternatively, the edge of the lens is shaped to fit eyeglass frames 170 before forming pattern 155 of optical elements 152 on lens 142. A second lens is modified in the same way to provide the second lens 151 for mounting in frames 170.

The process outlined in FIG. 1A can include additional steps. For example, Additional coatings can be applied to one or both of the lens surfaces either before or after application of pattern 155. Examples include UV or blue light filters, anti-reflective coatings, photochromic coatings, polarizers, mirror coatings, tints, and hardcoats. In some cases, additional shaping of a lens surface is performed, e.g., to customize a multifocal lens to the user either before or after application of pattern 155.

This process can be carried out at an optical store, distribution center, optical lab, or centralized manufacturing facility. Because the lens modification can be performed locally on lenses from a lens inventory, and in coordination with existing eyeglass dispensing protocols, Just-in-Time delivery of a highly customized pair of eyeglasses that includes a pattern of optical elements, such as a customized pattern of optical elements, is possible.

Referring also to FIG. 1B, in some implementations, personalized eyeglasses 101 are provided by a sequence 180 that may be performed entirely at the eye care professional's office or in concert with a distribution center, optical lab, or centralized manufacturing facility. In a first step 181, the eye care professional determines the patient's prescription, e.g., by refracting the subject. This step determines the power of the ophthalmic lens upon which the pattern is formed. The patient also chooses their eyeglass frames in the same way they would for regular prescription glasses. In some embodiments, eyeglass frames may be chosen from a retail store, and the lens shape can be communicated to the edging location by (i) providing a model number so that the trace shape can be retrieved from a database; (ii) performing a frame trace process at the store and providing the trace shape electronically; or (iii) shipping the frame to the edging location so that the edging facility can obtain the trace shape. In an alternative embodiment, eyeglass frames may be chosen from a "static frameboard", where one or more in-store models match eyeglass frames in inventory at the edging facility.

The eyecare professional can also gather additional information for selecting the pattern. Generally, the pattern can take into account factors such as a lens prescription (Rx) for the patient, a pupil size of the patient, a vergence of the patient, a pupillary distance of the patient, a gaze angle of the patient, a measure of myopic progression of the patient, a predisposition of the patient to myopia (e.g., a genetic predisposition or behavioral influence factors), the lens final shape and size once mounted to the spectacle frame, a measure of conspicuity of the pattern of optical elements to others, a measure of comfort level of the patient, an optical center height for a given pupil relative to a frame for the patient, a patient preference or choice (e.g., an outline shape of the pattern), and an eyecare professional's preference (e.g. dosage of treatment effect).

In the next step 182, the system identifies a pattern of optical elements suitable for the patient. This identification can include selecting from among several pre-established patterns (e.g., stored in a database of patterns) or calculating a new pattern according to a pattern generating algorithm. For example, the pattern can be calculated by the system to have a certain outline or density profile selected by the user.

Parameters for the pattern that can be varied include, for example, the type of optical element (e.g., lenslets, scattering centers, Fresnel lenses), a size of the optical elements, their density, and the shape of the area they occupy. Further parameters include a size, shape, and location of any clear apertures, as well as the location of the pattern on the lens. Each of these may be individualized depending on the desired optical effect of the pattern on the wearer (e.g., an amount of contrast reduction in the peripheral vision and clear aperture angular range) and/or the conspicuity of the pattern to someone else when an observer sees the eyeglasses being worn.

Once the system establishes the pattern, information about the pattern is transferred to the lens modification system, in step 183. This information can include one or more data files in a format readable by lens modification system 130. For example, commercial software suitable for generating images (e.g., Microsoft Office products such as Visio, PowerPoint, or Word; Adobe Photoshop, Adobe Illustrator) may be used in conjunction with standard driver software to generate control signals for the lens modification system 130. For example, the pattern can be specified in a file format such as WinLase Professional Job (WLJ), WinLase Professional Object (WLO), HPGL Plotter File (PLT), Windows Enhanced Metafile (EMF), Windows MetaFile (WMF), AutoCad (DXF), AutoCad (DWG), Adobe Illustrator (AI), CorelDRAW (CDR), Excellon2 File (EX2), Windows Bitmap (BMP), JPEG Bitmap (JPG), CompuServe Bitman (GIF), PaintBrush (PCX), TruView Job (JOB), or TruView Object (MCL) file. The pattern encoded in such a file could be generated using computer code, for example using a computer programming language such as AppleScript, JavaScript, Python, C++, and the like. Alternatively, or additionally, custom software and file formats can be used. Such a pattern can be generated by the software using input parameters from a specific user, such as an eyecare professional or a patient. Such a custom pattern can be generated in a short time that allows for rapid, Just-In-Time manufacturing, such as in 24 hours or less (e.g., 12 hours or less, 1 hour or less, 50 minutes or less, 40 minutes or less, 30 minutes or less, 20 minutes or less, 10 minutes or less, e.g., 1 minute or less, 40 second or less, 30 seconds or less, 10 seconds or less, 1 second or less).

Next, in step 184, the lens modification system 130 aligns the lens relative to the system or vice versa in order to form the pattern at the specified location on the lens. This can involve physically moving the lens with respect to the lens modification system and/or a software adjustment that translates, rotates, and/or scales the size of the pattern to accommodate the position of the lens. Once aligned, in step 185, the system modifies the lens according to the information about the pattern to form optical elements in the desired pattern.

In step 186, the lenses edges are shaped and the shaped lenses mounted in the frames.

In general, these steps can occur in other sequences. For example, the lenses could be edged and shaped in step 186 before the optical elements are formed on the lens in step 185.

In some embodiments, both the lens and the pattern are radially symmetric. In other words, the lens and patterns both have symmetry about a central axis. This can also be referred to as rotationally symmetric. For example, a plano lens or a lens having only spherical power, when provided with a circular edge, is a radially symmetric lens. In general, lenses having a circular edge are referred to as circular lenses, even though the curvature of the surfaces extend out of the plane of the circle defined by the edge.

Further, the optical elements can be arranged in a pattern that has radial symmetry about a geometric center of the pattern. Such patterns generally have a circular perimeter and, optically, perform the same function regardless of which radial direction the user looks through. In such cases, a geometric center of the pattern, such as the center of a clear aperture within an annular region of optical elements, can be aligned to the optical center of the lens. For such a spherical lens, the optical center often coincides with the geometric center of the lens. Alignment of the pattern to the lens in such cases can be achieved, for example, by measuring and marking the optical center using a lensometer and aligning the pattern with the marked optical center prior to forming the pattern on the lens.

Figure 1C:
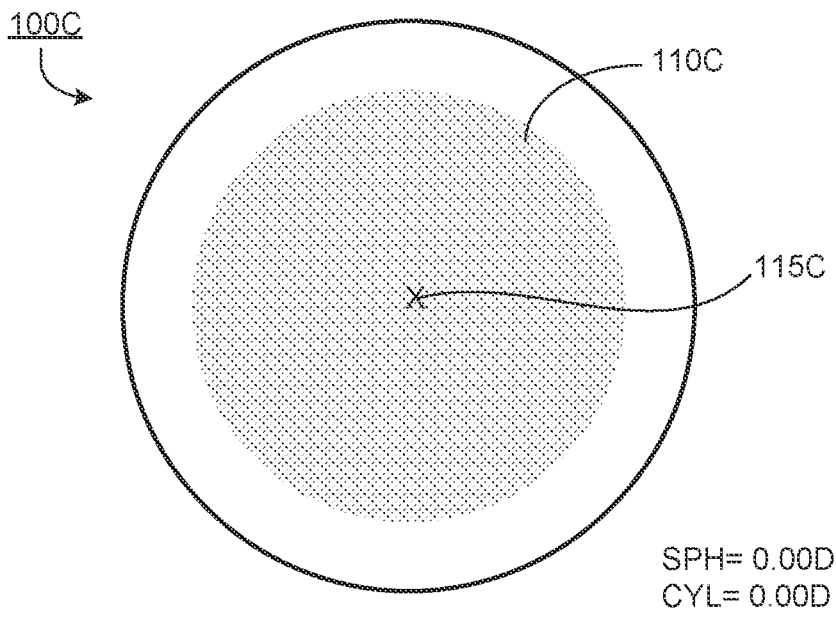
FIGS. 1C-1D are plan view diagrams showing examples of radially symmetric ophthalmic lenses with radially symmetric patterns.
Figure 1D:
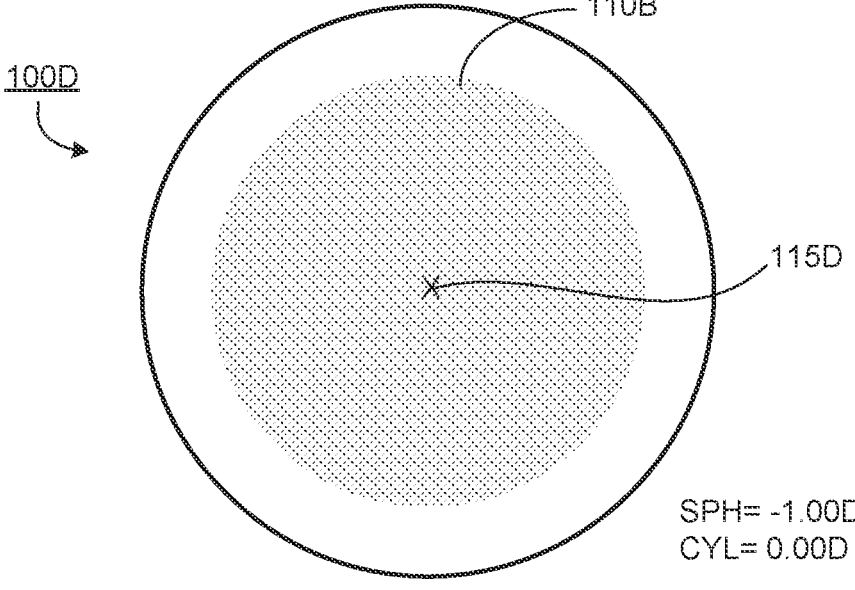

However, more generally, the foregoing techniques can also be used to form rotationally asymmetric patterns on radially symmetric or radially asymmetric lenses. Generally, this involves establishing a relative alignment between the lens and the pattern that accounts for the asymmetries before forming the optical elements. The system adjusts the alignment as necessary so that the relative alignment is as specified. In some embodiments, structural and/or optical alignment features can be formed on the lens that allow for alignment of the lens within the lens modification system before forming the optical elements. Examples are discussed below which generally fall within the following four categories:

Type 1: Radially Symmetric Lenses (e.g. with Radially Symmetric Power Profile) and radially symmetric patterns:
  (i) Circular, plano lens with a radially symmetric pattern centered on the lens. An example of such a lens is shown in FIG. 1C. Lens 100C is a plano lens (SPH=0.00 D, CYL=0.00 D) that includes a radially symmetric pattern 110C of optical elements centered on the geometric center 105C of the lens.
  (ii) Circular, spherical-powered lens without cylinder power with a radially symmetric pattern centered on the lens. An example of such a lens is shown in FIG. 1D. Here, lens 100D is a spherical-powered lens (SPH=−1.00 D, CYL=0.00 D) that includes a radially symmetric pattern 110D of optical elements centered on the geometric center 105D of the lens. Geometric center 105D coincides with the optical center of lens 100D.

In these examples, a lens can be made in "Just-In-Time" fashion by incorporating one or more inputs from the user, such as the density of the pattern, the spacing of the optical features, and the like. Such a lens does not require any orientation features; since it is radially symmetric in all respects, it can be shaped and mounted in any orientation. It is also possible to create such lenses in advance and keep them in inventory, with each pattern and spherical power being a separate stock keeping unit (SKU).

Type 2: Radially Asymmetric Lenses (e.g., with a Radially Asymmetric Power Profile) and Radially Symmetric Patterns (i) Circular, plano or circular, spherical-powered lens with a cylindrical power axis and a radially symmetric pattern centered on the lens. An example of such a lens is shown in FIG. 1E. A lens 100E having SPH=−1.00 D and CYL=−0.50 D along cylinder axis 102E includes a pattern 110E that is radially symmetric centered on the geometric center 105E of the lens.

(ii) Multi-focal or progressive lens with a radially symmetric pattern centered on the lens. An example of such a lens is shown in FIG. 1F, in which a progressive lens 100F has five zones of differing optical power (120F, 121F, 122F, 123F, and 124F). A radially symmetric pattern 110F is centered at the geometric center 105F of the lens.

(iii) Non-circular lens, such as a lens with flat edge or notch, or a lens that has been shaped to fit eyeglass frames, with a radially symmetric pattern centered on the lens. Examples of such lenses are shown in FIGS. 1G and 1H. In FIG. 1G, a lens 100G is circular but for a flat edge 101G. Lens 101G includes a radially symmetric pattern 110G that is centered at the radial center 105G of the circular portion of the edge of the lens. Center 105G may coincide with the optical center of the lens. FIG. 1H shows a lens 100H shaped to fit a pair of eyeglass frames. Lens 100H includes a radially symmetric pattern 110H with a center 105H that may coincide with the optical center of lens 100H.

In these examples, a lens can be made in "Just-In-Time" fashion by incorporating one or more inputs from the user, such as the density of the pattern, the spacing of the optical features, and the like. Such a lens does already have orientation features, but since the pattern is radially symmetric and centered on the lens, it does not require any specific orientation between the pattern and the lens. At the time of shaping, such a lens can be oriented using conventional optical alignment techniques, such as alignment using the cylindrical axis or using progressive lens markings. In some cases, such as a spherical-powered lens with cylindrical power, it is possible to create these lenses in advance and keep them in inventory, with each pattern and lens power being a separate stock keeping unit (SKU). In other cases, as with progressive lenses, this becomes impractical because of the large number of progressive designs that are normally customized to each patient. In this case, the pattern could first be applied to semi-finished blanks, which are held in inventory until the time of surfacing, or the pattern can be applied after surfacing in a "Just-In-Time" manner.

Figures 1I, 1J, 1K, 1L:
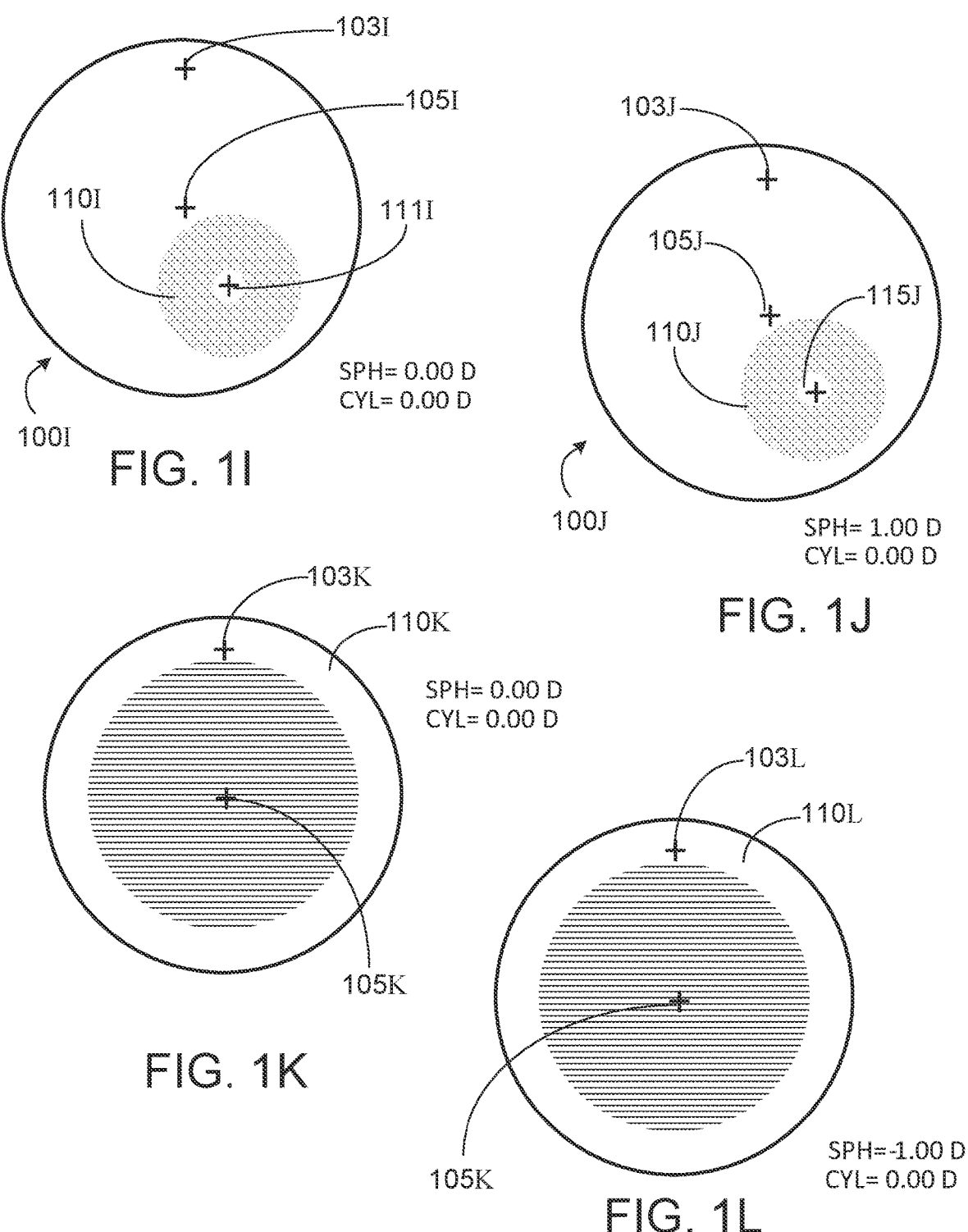
FIGS. 1I-1L are plan view diagrams showing examples of ophthalmic lenses radially symmetric lenses with radially asymmetric patterns.

Type 3: Radially Symmetric Lenses and Patterns Radially Asymmetric with Respect to Lens:

(i) Circular, plano lens with a radially symmetric pattern, with the center of the lens not matching geometric center of the pattern. FIG. 1I shows an example of such a lens. Here, a plano lens 100I includes a pattern 110I that is radially symmetric about a point 111I offset from a geometric center 105I of the lens. A marker 103I (e.g., on or within the lens) can be used as a fiducial when aligning the pattern with the lens.

(ii) Circular, spherical-powered lens without cylinder power with a radially symmetric pattern, with the center of the lens not matching geometric center of the pattern. FIG. 1J shows an example of such a lens. Specifically, a spherical lens 100J includes a pattern 110J that is radially symmetric about a point 111J offset from a geometric center 105J of the lens. The geometric center can coincide with the optical center of the lens. A marker 103J can be used as a fiducial when aligning the pattern with the lens.

(iii) Circular, plano lens with a radially asymmetric pattern. An example of such a lens is shown in FIG. 1K, where a plano lens 100K includes a pattern 110K having a circular outline by formed by horizontal lines of optical elements (e.g., rows of scattering centers or lenslets). The center of the circle of pattern 110K is aligned with the geometric center 105K of the lens. A marker 103K can be used as a fiducial when aligning the pattern with the lens.

(iv) Circular, spherical-powered lens without cylinder power with a radially asymmetric pattern. FIG. 1L shows an example of such a lens. Here, a spherical lens 100L includes a pattern 110L having a circular outline by formed by horizontal lines of optical elements (e.g., rows of scattering centers or lenslets). The center of the circle of pattern 110L is aligned with the geometric center 105L of the lens. The geometric center can coincide with the optical center of the lens. A marker 103L can be used as a fiducial when aligning the pattern with the lens.

In these examples, there is no need to align the lens for patterning since the starting lens is radially symmetric, but there needs to be an alignment mark added before, during, or after patterning to determine the desired orientation of the asymmetric pattern within the eyeglass frames. This alignment marker could be used for manual orientation, or read by a machine to determine orientation. It could also be used to place one or more additional orientation markers that, alone or with other markers, can be read manually or by a machine to determine the desired orientation. Examples of such alignment markers could be physical, such as a notch or flattened part of the circular outline of the lens, additional markings, such as fiducials or other alignment markers, or encoded/determined in the pattern asymmetry itself Type 4: Radially Asymmetric Lenses and Patterns Radially Asymmetric with Respect to Lens:

(i) Circular plano or spherical-powered lens with a cylindrical power axis and a radially symmetric pattern not centered on the lens. FIG. 1V shows an example of such a lens. Here, a lens 100V with SPH=−1.00 D, CYL=−0.50 D with cylinder axis 102V includes a pattern 110V of optical elements that is radially symmetric about a point 111V offset from a geometric center 105V of the lens.

(ii) Circular plano or spherical-powered lens with a cylindrical power axis and a radially asymmetric pattern. An example of such a lens is shown in FIG. 1M. Here, a lens 100M with SPH=−1.00 D, CYL=−0.50 D with cylinder axis 102M includes a pattern 110M having a circular outline formed by horizontal lines of optical elements (e.g., rows of scattering centers or lenslets).

The center of the circle of pattern 110M is aligned with the geometric center 105M of the lens.

(iii) Circular plano or spherical-powered lens, with or without cylindrical power axis, with a de-centered optical center, and a radially symmetric pattern not centered on the lens. FIG. 1N shows an example of such a lens. Here, a lens 100N includes a pattern 110N that is radially symmetric about a point 111N offset from a geometric center 105N of the lens. Point 111N coincides with the optical center of lens 100N.

(iv) Circular plano or spherical-powered lens, with or without cylindrical power axis, with a de-centered optical center, and a radially asymmetric pattern. FIG. 1O shows an example of such a lens. Here, a lens 100O includes a pattern 110O having a circular outline formed by horizontal lines of optical elements (e.g., rows of scattering centers or lenslets). The center of the circle of pattern 110O is aligned with the geometric center 105O of the lens but the optical center 111O of the lens is offset from the geometric center 105O.

Figures 1P, 1Q, 1R, 1S, 1T, 1U:
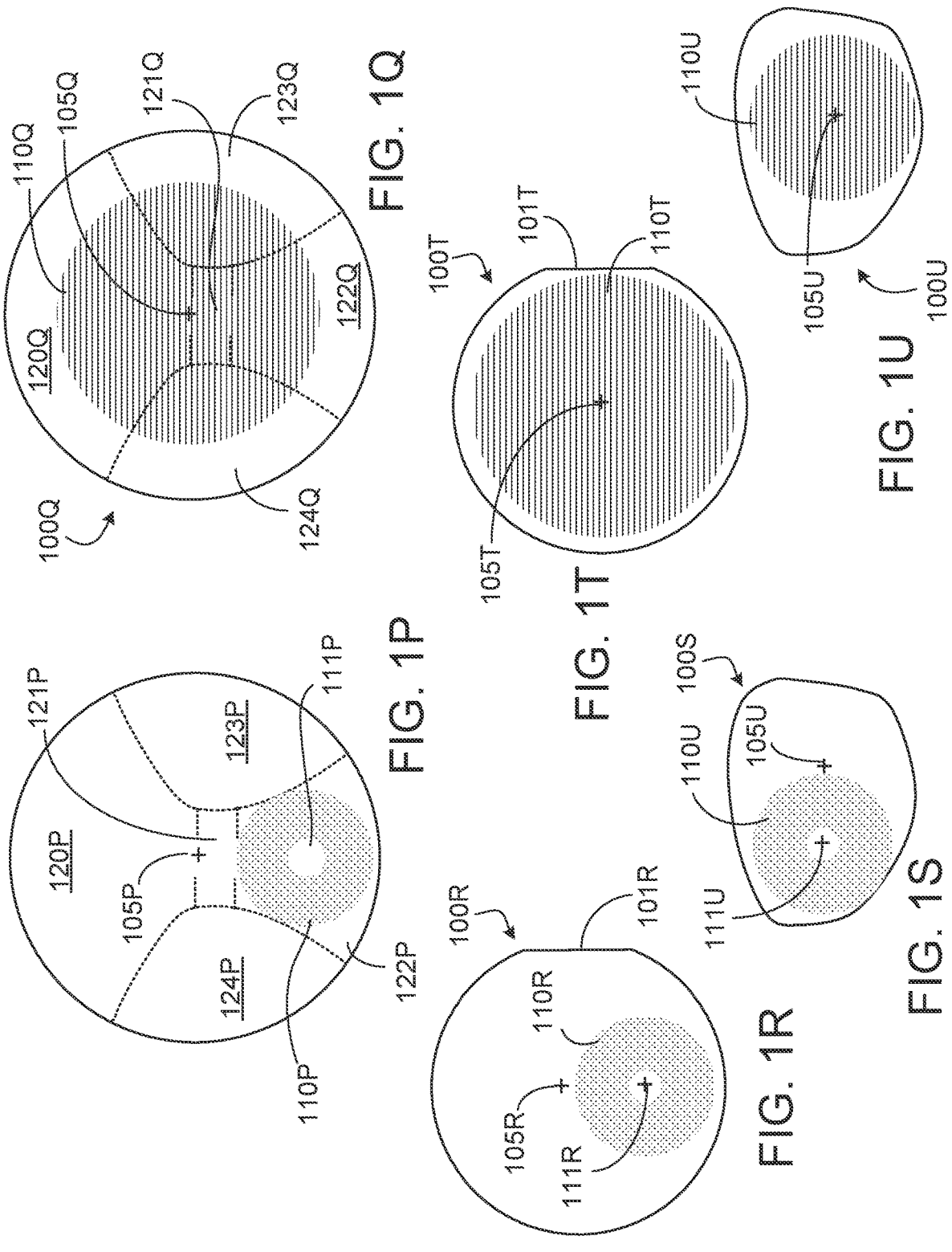

(v) Circular multifocal or progressive lens and a radially symmetric pattern not centered on the lens. FIG. 1P shows an example of such a lens. Here, a progressive lens 100P has five zones of differing optical power (120P, 121P, 122P, 123P, and 124P). A radially symmetric pattern 110P is centered at a point 111P that is in zone 122P and offset from the geometric center 105P of the lens which is located in zone 121P.

(vi) Circular multifocal or progressive lens and a radially asymmetric pattern, an example of which is shown in FIG. 1Q. Here, lens 100Q includes a pattern 110Q of optical elements arranged in parallel lines 120Q arranged horizontally across the lens, spanning zones (102Q, 103Q, 104Q, 105Q, and 106Q) of the lens have differing optical power. The radial center of pattern 110Q is aligned with the geometric center 105Q of lens 100Q.

(vii) Non-circular lens (such as a lens with flat edge or notch, or a lens that has been shaped to fit eyeglass frames) with a radially symmetric pattern not centered on the lens. FIG. 1R shows an example of such a lens 100R having a flat edge portion 101R and a pattern 110R of optical elements radially symmetric about a point 111R decentered from an optical center 105R of lens 100R. FIG. 1S shows an example of a lens 100S having an edge shaped to fit eyeglass frames. Lens 100S includes a pattern 1105 that is radially symmetric about a point 111S but not centered on the optical center 105S of the lens.

(viii) Non-circular lens (such as a lens with flat edge or notch, or a lens that has been shaped to fit eyeglass frames) with a radially asymmetric pattern. FIG. 1T shows an example of such a lens 100T having a flat edge portion 101T and a pattern 110T of optical elements with a circular outline. Pattern 110T is composed of horizontal rows of optical elements and the circle outlining the optical elements is centered on the optical center 105T of lens 100T. FIG. 1U shows an example of a lens 100U having an edge shaped to fit eyeglass frames. Lens 100U includes a pattern 110U of optical elements with a circular outline. Pattern 110U is composed of horizontal rows of optical elements and the circle outlining the optical elements is centered on the optical center 105U of lens 100U.

In these examples, both lens and pattern are radially asymmetric. In these cases, the orientation of the lens and the orientation of the pattern may be aligned so that, when the shaped lens is mounted into spectacle frames, both the lens and the pattern can be mounted according to the desired orientation. Because there is an almost unlimited number of lens designs, lens orientations, and pattern orientations, it would be difficult to manufacture and inventory such lenses in advance. There is, therefore, a great advantage in the Just-In-Time production of such lenses.

Figure 2:
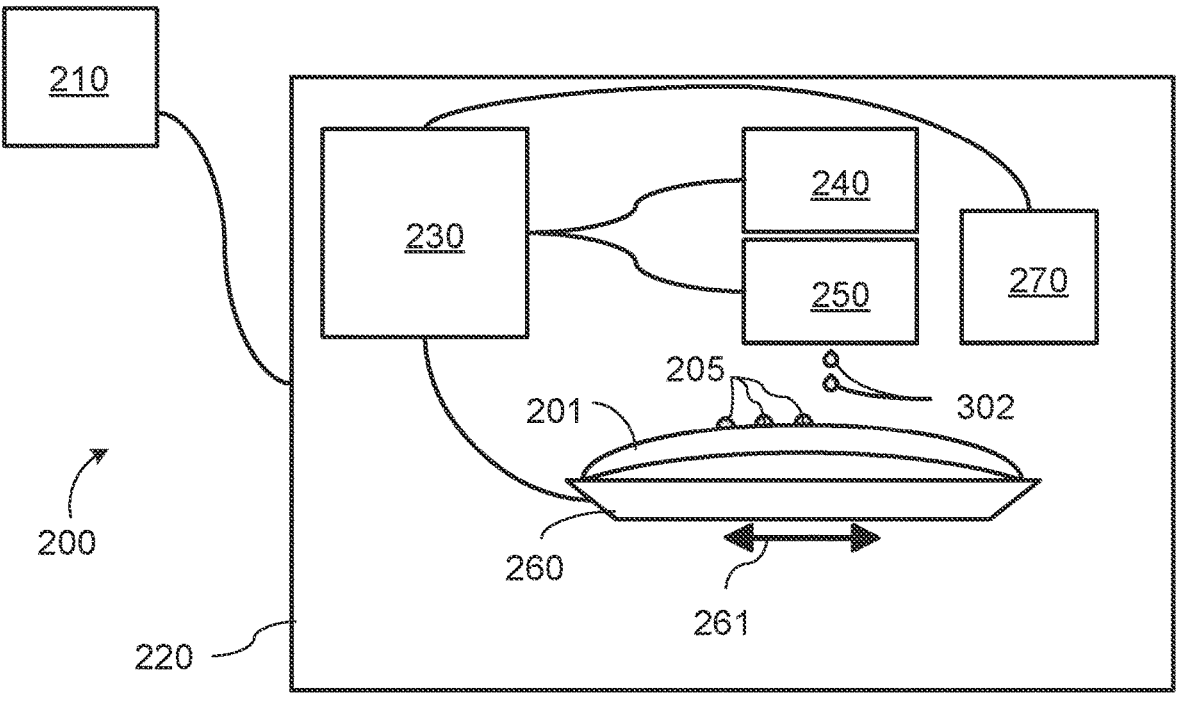
FIG. 2 is a schematic diagram of an example printing system for forming optical elements on a surface of an ophthalmic lens.

In general, optical elements can be formed on lenses in a variety of ways including UV LED Direct-to-Substrate Printing, pad printing, hot stamping and screen-printing technologies. Accordingly, a variety of different systems (e.g., commercially available systems) can be used for lens modification system 130 in system 100 described above. In some embodiments, optical elements are formed by inkjetting a curable material onto a surface of a blank ophthalmic lens and then curing the material to set the optical elements in the pattern. Referring to FIG. 2, an inkjetting and curing system 200 includes an inkjet printer 220 and a computer 210 in communication with the printer. Printer 220 includes a controller 230, a reservoir 240, an inkjet printhead 250, and a stage 260. Stage 260 supports a lens 201 and positions the lens relative to printhead 250. Reservoir 240 stores uncured material for inkjetting. Examples of curable material suitable for inkjetting includes various commercially available proprietary monomers and oligomers that are cross-linked together, by photopolymerization.

During operation, printhead 250 receives uncured material from reservoir 240. Stage 260 moves lens 201 relative to printhead 250 (as depicted by arrows 261) while printhead 250 ejects drops of uncured material 202 toward the lens. Either the stage and/or printhead may be the moving part during this process. Drop volume varies depending on the desired protuberance dimensions. Drop volumes may be in a range from 0.001 mm$^3$ to 0.05 mm$^3$ (e.g., about 0.002 mm$^3$, about 0.003 mm$^3$, about 0.004 mm$^3$, about 0.005 mm$^3$, about 0.006 mm$^3$, about 0.008 mm$^3$, about 0.010 mm$^3$, about 0.012 mm$^3$). Upon contact with the lens surface, the drops wet the surface forming uncured protuberances 305. Alternatively, in some embodiments, stage 260 remains stationary while actuators move the printhead relative to the lens.

System 200 also includes a UV lamp 270. Stage 260 positions the lens adjacent lamp 270 so that the lamp can cure the deposited material, forming the final protuberances. Examples of suitable UV lamps include LEDs emitting in the wavelength range of 360-390 nm. Alternatively. or in addition, thermal curing can be used to harden the deposited material.

Controller 230 is in communication with reservoir 240, printhead 250, stage 260, and UV lamp 270 and coordinates the operation of each to facilitate printing and curing of the drops. Specifically, controller 230 controls the relative motion between printhead 250 and stage 260, the inkjet drop ejection frequency, and drop volume so that system 200 forms the desired pattern on lens 201. Controller 230 may also control the temperature of the uncured material (e.g., by a heater associated with reservoir 240 or elsewhere) to control the viscosity of the uncured material. The user inputs the drop pattern via computer 210, which generates corresponding control signals for the printer and communicates the signals to controller 230.

Commercially available inkjet printers may be used. Suitable inkjet printers include Roland DGA (Irvine, CA) and Mimaki (Suwanee, GA) brands of UV LED Direct-to-Substrate Printers.

In some implementations, the lenses can be mounted in the frames and the frames fit to the wearer before the deposited material is cured. In this way, the printed pattern can be cleaned off the lens and the reprinted if necessary.

Other methods for forming optical elements composed of protrusions are also possible. For example, transfer or lithographic printing can be used instead of inkjetting. Transfer printing involves forming the protrusions on a different substrate and then transferring them to the surface of the lens in a separate process step. Lithographic printing may involve forming a continuous, uniform layer of the protrusion material on the lens surface and then patterning that layer to form the scattering center or lenslet pattern. Optical or contact lithography can be used to pattern the layer. In some embodiments, the pattern may be provided by a film that is laminated onto a surface of the lens.

While the optical elements formed by inkjet printing are protrusions formed on a surface of the ophthalmic lens, other implementations that provide comparable optical properties and lens durability are also possible. For example, in some embodiments, optical elements can be formed as recesses in a lens surface. The recesses can have dimensions similar to those of the protuberances described above. Recesses can be formed using a variety of techniques, such as etching (e.g., physical etching or chemical etching) or ablating material from the lens surface (e.g., using laser radiation or a molecular or ion beam).

In some embodiments, optical elements are formed on a lens surface by exposing the lens surface to laser radiation. Focused laser radiation locally interacts with the lens material at the surface, leaving a small depression, a bubble, a crater etc. By selectively exposing the lens surface to laser radiation, the optical element pattern can be formed on the surface. For example, the laser's beam can be moved relative to the surface while the beam is pulsed. Relative motion between the beam and the lens surface can be caused by moving the beam while leaving the surface fixed, moving the surface while leaving the beam fixed, or moving both the beam and the surface.

Figure 3:
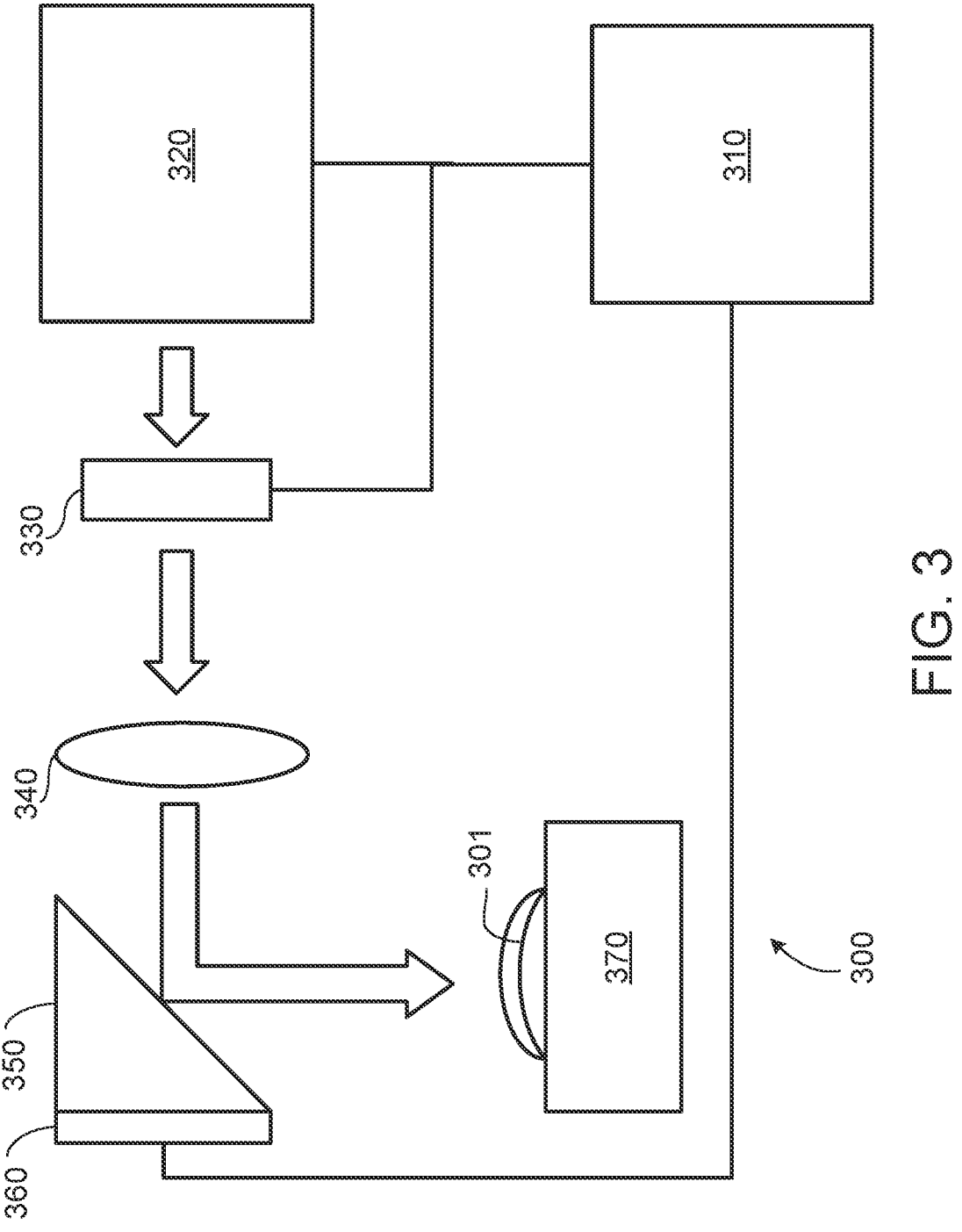
FIG. 3 is a schematic diagram of an example laser system for forming optical elements on an ophthalmic lens.

Referring to FIG. 3, an example laser system 300 for forming optical elements on a surface of a lens includes a laser 320, a beam chopper 330, focusing optics 340, a mirror 350, and a stage 370. Laser 320 directs a laser beam towards mirror 350, which deflects the beam towards a lens 301 which is positioned relative to the mirror 350 by stage 370. An actuator 360 (e.g., a piezoelectric actuator) is attached to mirror 350. Laser system 300 also includes a controller (e.g., a computer controller) in communication with laser 320, beam chopper 330, and actuator 360.

Beam chopper 330 and focusing optics 340 are positioned in the beam path. Chopper 330 periodically blocks the beam so that lens 301 is exposed to discrete pulses of laser light. Focusing optics 340, which generally includes one or more optically powered elements (e.g., one or more lenses), focuses the beam to a sufficiently small spot on the surface of lens 301 so that the area modified by the beam on the lens surface can be shaped to the desired pattern feature size. Actuator 360 changes the orientation of mirror 350 with respect to the beam to scan the pulsed beam to different target points on the lens surface. Controller 310 coordinates the operation of laser 320, chopper 330, and actuator 360 so that the laser system forms the predetermined optical element pattern on the lens.

In some implementations, stage 370 also includes an actuator. The stage actuator can be a multi-axis actuator, e.g., moving the lens in two lateral dimensions orthogonal to the beam propagation direction. Alternatively, or additionally, the actuator can move the stage along the beam direction. Moving the stage along the beam direction can be used to maintain the exposed portion of the lens surface at the focal position of the beam, notwithstanding the curvature of the lens surface, thereby maintaining a substantially constant beam size across the lens surface. The stage actuator can also be controlled by controller 310, which coordinates this stage motion with the other elements of the system. In some embodiments, a stage actuator is used in place of the mirror actuator.

Furthermore, in some implementations, the orientation and position of optical or structural features of the lens is captured using, e.g., a focimeter, lensometer, optical mapper, CCD camera with feature detection software, mechanical fixture or tracer to catch on mechanical structure, etc. before introduction to the system 100 or 200, respectively. The lens is then held in place in a known orientation and position based on the previous measurement using, e.g., clamps, fixtures, jigs, suction cups, etc. and is introduced into the system 100 or 200, respectively, without losing the orientation and position information. This transfer can be effectuated, e.g., by use of robotic arms, manual transfer into a holder or known position and orientation, rotary turntable with fixed locking positions, etc. Alternatively, the apparatus for capturing orientation and position of optical and structural features of the lens, including the aforementioned examples, can be integrated with other components of the system, e.g., in an actuated stage 260 or 370, conveyor or a rotary table. In general, implementations can include machine vision and automated alignment of the lens to various system components to achieve the desired placement of the pattern of optical elements on the lens.

Generally, laser 320 can be any type of laser capable of generating light with sufficient energy to modify the lens material at the surface. Gas lasers, dye lasers, solid state lasers, and semiconductor lasers can be used. Generally, many laser technologies suitable for, e.g., machining applications can be used. Gas lasers include certain excimer lasers (e.g., XeCl at 308 nm) and XeF at 353 nm). Another kind of gas laser that can be used include certain infrared lasers, such as a $CO_2$ laser (having an emission wavelength at 9.4 μm or 10.6 μm) can be used. Commercially available laser systems can be used such as, for example, $CO_2$ laser systems made by Universal Laser Systems, Inc. (Scottsdale, AZ), (e.g., the 60 W VLS 4.60 system). Examples of solid state lasers that can be used include Ytterbium-doped glass lasers emitting at 1 μm and chromium-doped alexandrite lasers (e.g., emitting visible or near IR wavelengths). Examples of semiconductor lasers that may be used include InGaAsP or InGaAsP lasers.

The pulse duration and pulse energy are typically selected to modify an amount of material at the lens surface to provide an optical element of a desired size.

While the foregoing example lens modifications systems involve forming optical elements on the lens surface, alternatively, or additionally, optical elements can be embedded in the lens material itself. For example, the lens material and laser exposure system can be selected so that the exposure causes a local change in the refractive index of the bulk lens material itself, forming optical elements (e.g., scattering centers or lenslets) in the body of the lens. Further methods for forming optical elements on a lens are described in Appendix I and Appendix II, enclosed herewith.

Figure 4:
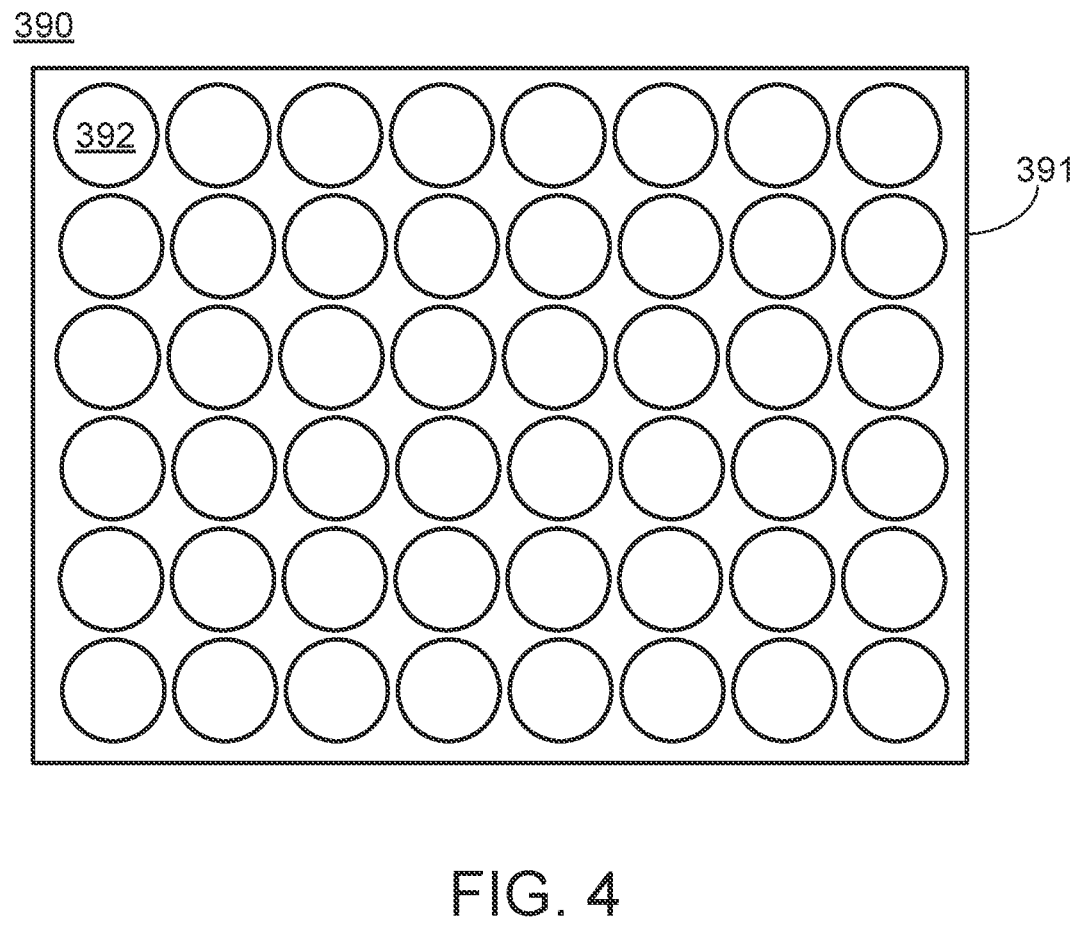

Referring to FIG. 4, in some implementations, a jig 490 is used to support multiple lenses during lens modification. Jig 490 includes a tray 491 that features an array of lens holders 492 on one surface, each sized to securely hold a lens. For example, if 70 mm diameter lens blanks are used, the lens holders each have a diameter of 70 mm to tightly hold a respective lens. During operation, jig 490 including one or more lenses is positioned on stage 460. Alternatively, smaller (e.g., 60 mm) or larger (e.g., 80 mm or 100 mm) lens blanks can be used. The jig holds each lens in precise location so that system 400 can accurately jet or laser irradiate onto the lenses' surface. In addition, the jig allows for manufacturing multiple lenses per batch. While the jig in FIG. 4 includes 48 lens holders, generally, jigs can be designed to hold any number of lenses subject to the physical constraints imposed by the lens modification system. Many sizes of jigs are possible, for example jigs that accommodate about 24 lenses, about 48 lenses, about 100 lenses, about 200 lenses, about 300 lenses, about 400 lenses, about 500 lenses, or more than 500 lenses per run.

Figure 5:
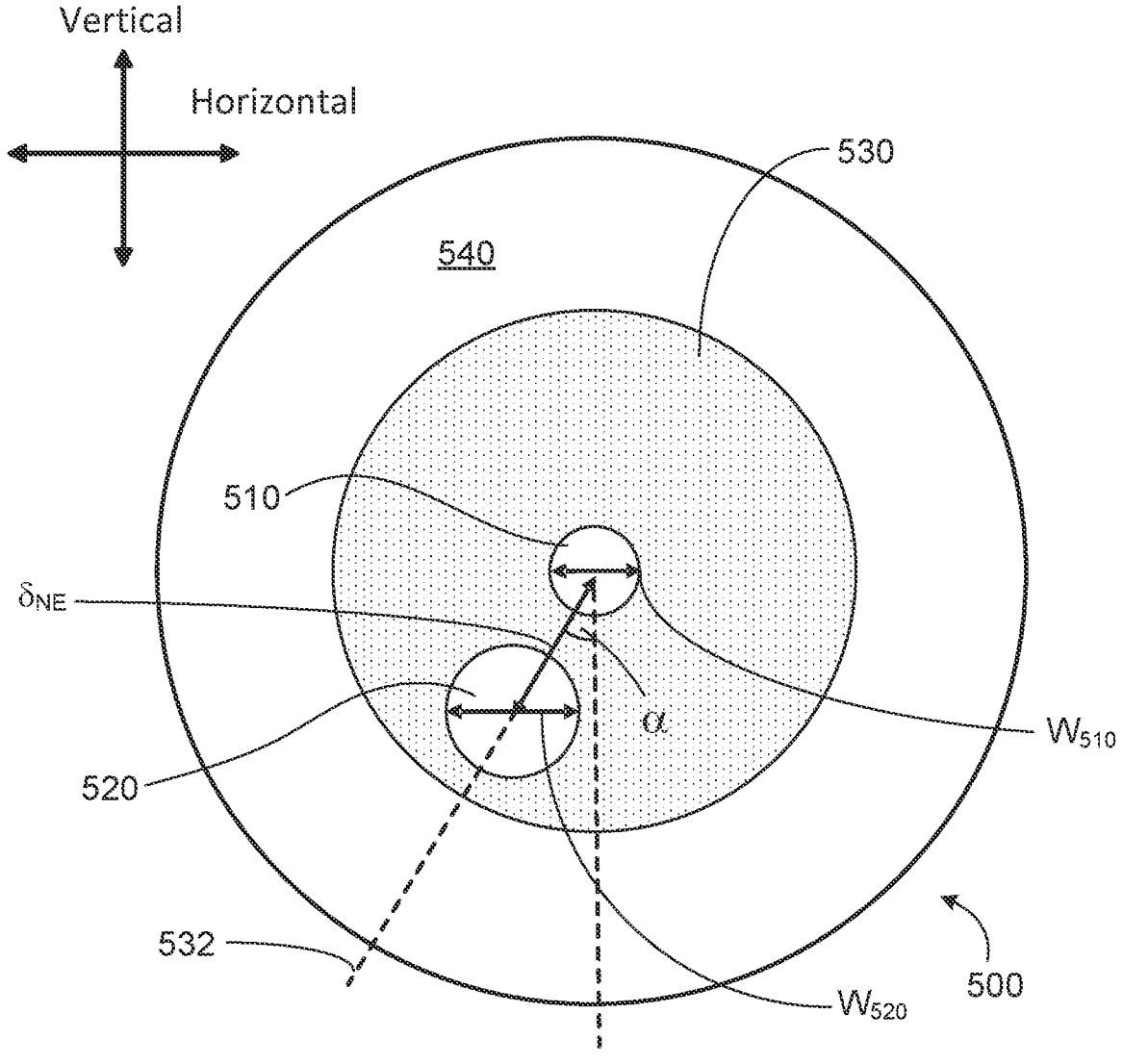
FIG. 5 is a plan view diagram of an example ophthalmic lens with a pattern of optical elements that includes two clear apertures.

Turning now to further examples of optical element patterns, in general, a variety of different patterns are possible. As noted above, in some embodiments, rotationally asymmetric patterns are used. Such patterns lack radial symmetry about an axis, such as an axis running through a geometry center of the pattern. An example of such a pattern is illustrated in FIG. 5, which shows an ophthalmic lens 500 includes a first clear aperture 510 and an annular shaped scattering area 530 surrounding the clear aperture. In this case, the lens 500 has uniform optical properties, e.g., is a single vision lens, such as a spherical lens or a compound or toric lens (i.e., having a spherical component and a cylindrical component), or a plano lens (i.e., a lens with no optical power). FIG. 5 also shows a vertical and horizontal axis for ease of reference. While lens 500 is depicted as a circular blank, and therefore radially symmetric for a spherical lens, it will be understood that the horizontal and vertical directions refer to how the lens will be oriented when mounted in glasses frames.

First clear aperture 510 is positioned substantially near the center of lens 500. Patterned area 530 is also centered with respect to the lens center. Patterned area 530 is also surrounded by a clear area 540. A second clear aperture 520 is also provided in patterned area 530, separated from clear aperture 510 along an axis 532 that is offset by an angle α from the vertical axis of the lens.

In the embodiment show in FIG. 5, clear aperture 510 is a distance vision aperture, which can be engaged for distance-vision activities such as reading road signs. The second clear aperture 520 is a near vision aperture, which can be engaged for near-vision activities, such as reading a book.

When a refers to the offset angle from the vertical meridian once mounted, it can be selected to accommodate the path of the user's eye when they focus on near objects. When a person accommodates to focus on near objects, this also creates convergence, or the movement of the eyes inward in the horizontal direction, called vergence. Therefore, in order to make near-vision objects visible to the accommodated eye through the second aperture, the angle can be chosen to match a user's vergence for near objects. In some embodiments, α is 45° or less, e.g., about 30° or less, about 25° or less, about 20° or less, about 15° or less, about 10° or less, about 8° or less, e.g., 1° or more, 2° or more, 3° or more, 4° or more, 5° or more, or 0°. For example, the clear aperture 520—for near-vision—can be offset from the vertical axis that passes through the center of clear aperture 510 toward the user's nose in order to accommodate for vergence of the wearer's eyes as they focus on near objects. This offset can be 1 mm or more (e.g., 2 mm or more, 3 mm or more, 4 mm or more, 5 mm or more, 6 mm or more, 7 mm or more, such as 10 mm or less, 9 mm or less, 8 mm or less), where the distance is measured from the central point in the horizontal direction of clear aperture 520 from the central point in the horizontal direction of clear aperture 510 (which may correspond to the center of the lens, in some embodiments). Both clear aperture 510 and clear aperture 520 are circular in shape, with aperture 520 having a slightly larger diameter than aperture 510. Generally, the size of the apertures can vary and are set so that they provide the user with adequate on-axis vision (through aperture 510) and adequate near-vision (through aperture 520) while not being so large as to significantly impede the effect of the contrast reduction in peripheral vision due to the optical elements in the patterned area. Typically, both clear apertures have diameters of 2 mm or more (e.g., 3 mm or more, 4 mm or more, 5 mm or more, such as 10 mm or less).

Non-circular apertures are also possible (see below for specific examples). For instance, the horizontal width of an aperture can be different from a vertical height of the apertures. In FIG. 5, the horizontal widths of apertures 510 and 520 are designated $w_{510}$ and $w_{520}$, respectively. Generally, the horizontal widths of the apertures can be the same or different. In some embodiments, such as illustrated in FIG. 5, $w_{520}$ can be larger than $w_{510}$. For example, $w_{520}$ can be 10% or more larger than $w_{510}$ (e.g., 20% or more, 30% or more, 40% or more, 50% or more, 75% or more, 100% or more, such as 200% or less, 150% or less, 120% or less). In some embodiments, the $w_{520}$ is selected so that, for near vision, the user's visual axis stays within the clear aperture 520 while the user is engaged with a specific task during which their eye horizontally scans a visual field (e.g., while reading). This can be advantageous where it allows the user to scan the visual field through the clear aperture without having to move their head.

The distance between the apertures can also vary and is typically set so that the apertures correspond to comfortable on-axis vision and comfortable near-vision for the user. The distance between the closest edges of the clear apertures can be 1 mm or more (e.g., 2 mm or more, 5 mm or more, such as 10 mm or less).

A distance between the centers of aperture 510 and aperture 520, denoted $\delta_{NF}$ in FIG. 5, can vary so that aperture 520 corresponds to gaze direction of the user when focused on near objects. In some embodiments, $\delta_{NF}$ can be in a range from 0.5 mm to 20 mm (e.g., 0.6 mm or more, 0.7 mm or more, 0.8 mm or more, 0.9 mm or more, 10 mm or more, 11 mm or more, 12 mm or more, 13 mm or more, 14 mm or more, e.g., 19 mm or less, 18 mm or less, 17 mm or less, 16 mm or less, 15 mm or less).

The separation between aperture 510 and aperture 520 depends on the size of each aperture and the distance between their centers. In some embodiments, this separation can be 0.5 mm or more (e.g., 1 mm or more, 2 mm or more, 3 mm or more). The separation can be less than 10 mm (e.g., 9 mm or less, 8 mm or less, 7 mm or less, 6 mm or less, 5 mm or less).

Patterned area 530 includes optical elements which scatter at least some of the light incident on the lens in these areas or which defocus or blur through optical aberrations. This can reduce contrast of the peripheral vision of a user, which is believed to reduce development of myopia in a user. Generally, optical elements can include features (e.g., protrusions or depressions) on a surface of the lens or inclusions in the bulk lens material.

In general, the nature of the optical elements can be selected based on a variety of design parameters to provide a desired degree of contrast reduction on the user's retina. Generally, these design parameters include the optical element density, their size and shape, and their refractive index, for example, and are discussed in more detail below. Ideally, the optical elements are selected to provide high visual acuity on the fovea and reduced image contrast on other parts of the retina with sufficiently low discomfort to the wearer to allow for extended, continuous wear. For instance, it can be desirable for children to be comfortable wearing the eyeglasses for most, if not all, of a day. Alternatively, or additionally, optical elements can be designed for specific tasks, especially tasks which are believed to strongly promote eyelength growth, e.g., video gaming, reading or other wide angle, high contrast image exposure. For example, in such situations (e.g., where the user experiences high contrast in their peripheral vision and/or situations that do not require the wearer to move and to orient themselves using peripheral vision), the scattering intensity and scatter angle in the periphery can be increased, while considerations of consciousness and self-esteem may be less of a concern. This can lead to a higher efficiency in peripheral contrast reduction in such high contrast environment. Similarly, the blur radius and intensity of defocusing lenslets or optical aberration features can be tailored.

It is believed that reduced image contrast on the fovea of the user's eye is less efficient at controlling eye growth than reducing image contrast on other parts of the user's retina. Accordingly, the scattering centers can be tailored to reduce (e.g., minimize) light scattered into the user's fovea, while relatively more of the light on other parts of the retina is scattered light. The amount of scattered light on the fovea can be affected by the size of the clear apertures, but also by the nature of the scattering centers, especially those closest to the clear apertures. In some embodiments, for example, the scattering centers closest to the clear apertures can be designed for less efficient light scattering than those further away. Alternatively, or additionally, in some embodiments scattering centers closest to the clear apertures can be designed for smaller angle forward scattering that those further from the aperture. In a similar fashion, the amount of blur generated by defocusing lenslets or optical aberration features is dependent on density of the features, their size and intensity of visual blurring, e.g., by the amount of relative plus add-power of lenslets). Design optimization to reduce blurring in central vision while inducing blur in the peripheral retinal region enables a comfortable visual experience, while reducing the progression of myopia.

In certain embodiments, scattering centers can be designed to deliver reduced narrow angle scattering and increased wide angle scattering through geometry of scattering centers to create even light distribution on retina/low contrast signal, while preserving visual acuity. For example, the scattering centers can be designed to generate significant wide forward angle scattering (e.g., such as more than 10%, 20% or more, 30% or more, 40% or more, 50% or more, deflected by more than 2.5 deg.). Narrow angle forward scattering, i.e., within 2.5 deg., can be kept relatively low (e.g., 50% or less, 40% or less, 30% or less, 20% or less, 10% or less).

In general, a variety of different metrics can be used to evaluate the performance of scattering centers in order to optimize them for use in myopia reducing eyeglasses. For example, scattering centers can be optimized empirically, e.g., based on physical measurements of lenses with different scattering centers shapes, sizes, and layouts. For example, light scattering can be characterized based on haze measurements, such as international test standards for haze (e.g., ASTM D1003 and BS EN ISO 13468). Conventional hazemeters can be used, e.g., a BYK-Gardner haze meter (such as the Haze-Gard Plus instrument) that measures how much light is totally transmitted through a lens, the amount of light transmitted undisturbed (e.g., within 0.5 deg.), how much is deflected more than 2.5 deg., and clarity (amount within 2.5 deg.), which can be considered a measure for narrow angle scattering. Other equipment can also be used to characterize light scattering for purposes of empirically optimizing scattering patterns. For example, equipment that measures light diffusion by measuring light in annular ring around 2.5 deg. can be used (e.g., equipment from Hornell described in standard EN 167).

Alternatively, or additionally, contrast reducing optical elements can be optimized by computer modelling software (e.g., Zemax or Code V).

In some embodiments, scattering centers can be designed based on optimization of a point spread function, which is a representation of an image of the scattering center on the retina. For example, the size, shape, composition, spacing and/or refractive index of the scattering centers can be varied to evenly spread illumination of retina such that the retina outside of fovea is homogeneously blanketed with scattered light to reduce (e.g., minimize) contrast at this region of the retina.

In some embodiments, the optimization of light scattering blanketing the peripheral retina accentuates the intensity of scattered light vs. undisturbed light in certain areas of the retina to more strongly suppress high contrast images. High contrast images, e.g., reading black and white text, tend to stem more from the lower half of the visual orbit. Therefore, a stronger blanketing of the upper retinal orbit with scattered light can be beneficial to reduce the signal for axial length growth, while reducing the visual impact, e.g., glare or halos, on the upper visual orbit. Similarly, blur from defocusing lenslets or optical aberration features can be modified in intensity to influence lower and upper part of the visual orbit differently.

Alternatively, or additionally, scattering centers can be designed based on optimization of a modulation transfer function, which refers to the spatial frequency response of the human visual system. For instance, the size, shape, and spacing of the scattering centers can be varied to smoothen attenuation of a range of spatial frequencies. Design parameters of the scattering centers can be varied in order to increase or decrease certain spatial frequencies as desired. Generally, the spatial frequencies of interest for vision are 18 cycles per deg. on the fine side, and 1.5 cycles per deg. on the course side. Scattering centers can be designed to provide increased signal at certain subsets of spatial frequencies within this range.

The aforementioned metrics can be used to evaluate scattering centers based on the size and/or shape of the scattering centers, both of which can be varied as desired. For example, the scattering centers can be substantially round (e.g., spherical), elongate (e.g., ellipsoidal), or irregularly shaped. Generally, where scattering centers are protuberances on a surface of the lens, the protuberances should have a dimension (e.g., diameter) that is sufficient large to scatter visible light, yet sufficiently small so as not to be resolved by the wearer during normal use. For example, the scattering centers can have a dimension in a range from about 0.001 mm or more (e.g., about 0.005 mm or more, about 0.01 mm or more, about 0.015 mm or more, about 0.02 mm or more, about 0.025 mm or more, about 0.03 mm or more, about 0.035 mm or more, about 0.04 mm or more, about 0.045 mm or more, about 0.05 mm or more, about 0.055 mm or more, about 0.06 mm or more, about 0.07 mm or more, about 0.08 mm or more, about 0.09 mm or more, about 0.1 mm) to about 1 mm or less (e.g., about 0.9 mm or less, about 0.8 mm or less, about 0.7 mm or less, about 0.6 mm or less, about 0.5 mm or less, about 0.4 mm or less, about 0.3 mm or less, about 0.2 mm or less, about 0.1 mm).

Note that for smaller scattering centers, e.g., having a dimension that is comparable to the wavelength of light (e.g., 0.001 mm to about 0.05 mm), the light scattering may be considered Raleigh or Mie scattering. For larger scattering centers, e.g., about 0.1 mm or more, light scattering may be mostly due to geometric scattering. Optical elements may also include, for example, non-focusing lenslets, prisms, or higher-order aberration lenslets.

In general, the dimension of the optical elements may be the same across each lens or may vary. For example, the dimension may increase or decrease as a function of the location of the optical element, e.g., as measured from the clear aperture and/or as a function of distance from an edge of the lens. In some embodiments, the optical element dimensions vary monotonically as the distance from the center of the lens increases (e.g., monotonically increase or monotonically decrease). In some cases, monotonic increase/decrease in dimension includes varying the diameter of the optical element linearly as a function of the distance from the center of the lens.

The shape of optical elements can be selected to provide an appropriate light scattering or blur profile. For example, the optical elements can be substantially spherical or aspherical. In some embodiments, optical elements can be elongated in one direction (e.g., in the horizontal or vertical direction), such as in the case of elliptical scattering centers. In some embodiments, the optical elements are irregular in shape.

Generally, the distribution of optical elements in patterned area 530 can vary to provide an appropriate level of light scattering or blur. In some embodiments, the optical elements are arranged in a regular array, e.g., on a square grid, spaced apart by a uniform amount in each direction. In general, the optical elements are spaced so that, collectively, they provide sufficient contrast reduction in the viewer's periphery for myopia reduction. Typically, smaller spacing between scattering centers will result in greater contrast reduction (provided adjacent scattering centers do not overlap or merge). In general, scattering centers can be spaced from their nearest neighbor by an amount in a range from about 0.05 mm (e.g., about 0.1 mm or more, about 0.15 mm or more, about 0.2 mm or more, about 0.25 mm or more, about 0.3 mm or more, about 0.35 mm or more, about 0.4 mm or more, about 0.45 mm or more, about 0.5 mm or more, about 0.55 mm or more, about 0.6 mm or more, about 0.65 mm or more, about 0.7 mm or more, about 0.75 mm or more) to about 2 mm (e.g., about 1.9 mm or less, about 1.8 mm or less, about 1.7 mm or less, about 1.6 mm or less, about 1.5 mm or less, about 1.4 mm or less, about 1.3 mm or less, about 1.2 mm or less, about 1.1 mm or less, about 1 mm or less, about 0.9 mm or less, about 0.8 mm or less). As an example, spacing can be 0.55 mm, 0.365 mm, or 0.240 mm.

Optical elements may be arrayed in grids that are not square. For example, hexagonal (e.g., hexagonally close packed) grids may be used. Non-regular arrays are also possible, e.g., random or semi-random placement may be used. Displacement from square grids or hexagonally packed grids is also possible, e.g., by a randomized amount. Examples of such optical element patterns are shown in Appendix II.

In general, the coverage of a lens by optical elements can vary depending on the pattern. Here, coverage refers to the proportion of the lens's total area, as projected onto the plane shown in FIG. 5 that corresponds to an optical element. Typically, a lower optical element coverage will yield lower scattering or blur than higher coverage (assuming individual optical elements are discrete, i.e., they do not merge to form larger optical elements). Scattering center coverage can vary from 5% or more to about 75%. For example, coverage can be 10% or more, 15% or more, 20% or more, 25% or more, 30% or more, 35% of more, 40% or more, 45% or more, such as 50% or 55%). Coverage can be selected according to a comfort level of a user, e.g., to provide a level of peripheral vision sufficiently comfortable that the wearer will voluntarily wear the eyeglasses for extended periods (e.g., all day) and/or according to the desired intensity with which the axial eye length growth signal is suppressed.

It is believed that light from a scene that is incident on the lens in scattering area 530 between the optical elements contributes to a recognizable image of the scene on the user's retina, while light from the scene incident on the optical elements does not necessarily. Moreover, at least some of the light incident on the optical elements is transmitted to the retina, so has the effect of reducing image contrast without substantially reducing light intensity at the retina. Accordingly, it is believed that the amount of contrast reduction in the user's peripheral field of view is correlated to (e.g., is approximately proportional to) the proportion of the surface area of the reduced-contrast areas covered by the optical elements.

In general, the scattering centers are intended to reduce the contrast of images of objects in the wearer's peripheral vision without significantly degrading the viewer's visual acuity in this region. For example, the scattering centers can scatter predominantly into wide angles. Here, peripheral vision refers to the field of vision outside of the field of the clear aperture. Image contrast in these regions can be reduced by 40% or more (e.g., 45% or more, 50% or more, 60% or more, 70% or, more, 80% or more) relative to an image contrast viewed using the clear aperture of the lens as determined using methods discussed below. Contrast reduction can be measured by contrast sensitivity loss of one or more letters, or one or more lines, on a high contrast or low contrast visual acuity eye chart, such as a Snellen chart or ETDRS eye chart. Contrast reduction could be one letter or more, 2 letters or more, 3 letters or more, 4 letters or more, or 5 letters or more, or could be one line or more, two lines or more, or three lines or more. Contrast reduction could also be less than a certain amount, such as three lines or less, two lines or less, one line or less; or five letters or less, 4 letters or less, 3 letters or less, 2 letters or less, or one letter; all as measured on a high contrast or low contrast visual acuity eye chart. Contrast reduction may be set according to the needs of each individual case. It is believed that a typical contrast reduction would be in a range from about 50% to 55%. Contrast reductions of lower than 50% may be used for very mild cases, while subjects who are more predisposed might need a higher than 55% contrast reduction. Visual acuity can be corrected to 20/30 or better (e.g., 20/25 or better, 20/20 or better) as determined by subjective refraction, while still achieving meaningful contrast reduction. In embodiments, contrast reduction can result in loss of two or fewer Snellen chart lines (e.g., 1.5 or fewer lines, one line or less), where one line of loss corresponds to a visual acuity drop from 20/20 to 20/25.

Contrast, here, refers to the difference in luminance between two objects within the same field of view. Accordingly, contrast reduction refers to a change in this difference.

Contrast and contrast reduction may be measured in a variety of ways. In some embodiments, contrast can be measured based on a brightness difference between different portions of a standard pattern, such as a checkerboard of black and white squares, obtained through the clear aperture and scattering center pattern of the lens under controlled conditions.

Alternatively, or additionally, contrast reduction may be determined based on the optical transfer function (OTF) of the lens (see, e.g., http://www.montana.edu/jshaw/documents/18%20EELE582_S15_OTFMTF .pdf). For an OTF, contrast is specified for transmission of stimuli in which light and dark regions are sinusoidally modulated at different "spatial frequencies." These stimuli look like alternating light and dark bars with the spacing between bars varying over a range. For all optical systems the transmission of contrast is lowest for the sinusoidally varying stimuli having the highest spatial frequencies. The relationship describing the transmission of contrast for all spatial frequencies is the OTF. The OTF can be obtained by taking the Fourier transform of the point spread function. The point spread function can be obtained by imaging a point source of light through the lens on to a detector array and determining how light from a point is distributed across the detector.

In the event of conflicting measurements, the OTF technique is preferred. In some embodiments, contrast may be estimated based on the ratio of the area of the lens covered by scattering centers compared to the area of the clear apertures. In this approximation, it is assumed that all the light that hits the scattering centers becomes uniformly dispersed across the entire retinal area, which reduce the amount of light available in lighter areas of an image and this adds light to darker areas. Accordingly, contrast reduction may be calculated based on light transmission measurements made through the clear apertures and scattering area of a lens.

Patterned area 530 has a circular shape, although other shapes are also possible (e.g., elliptical, polygonal, or other shape, such as irregular shapes including images). The size of patterned area is typically selected so that reduced contrast of the user's peripheral vision is experienced over a substantial part of the user's visual field, even when not looking directly through the on-axis aperture. Patterned area 530 can have a diameter (or maximum dimension, for non-circular areas) of 30 mm or more (e.g., 40 mm or more, 50 mm or more, 60 mm or more, 70 mm or more, 80 mm or more e.g., 100 mm or less, 90 mm or less, 80 mm or less, 70 mm or less, 60 mm or less). In some embodiments, the patterned area extends to the edge of the lens.

In some embodiments the periphery of the patterned area can be blended with the clear area by gradually reducing the optical element amount, density or power.

In some embodiments the clear area can exhibit a lower amount of light scattering or blur compared to the patterned area.

Figure 6A:
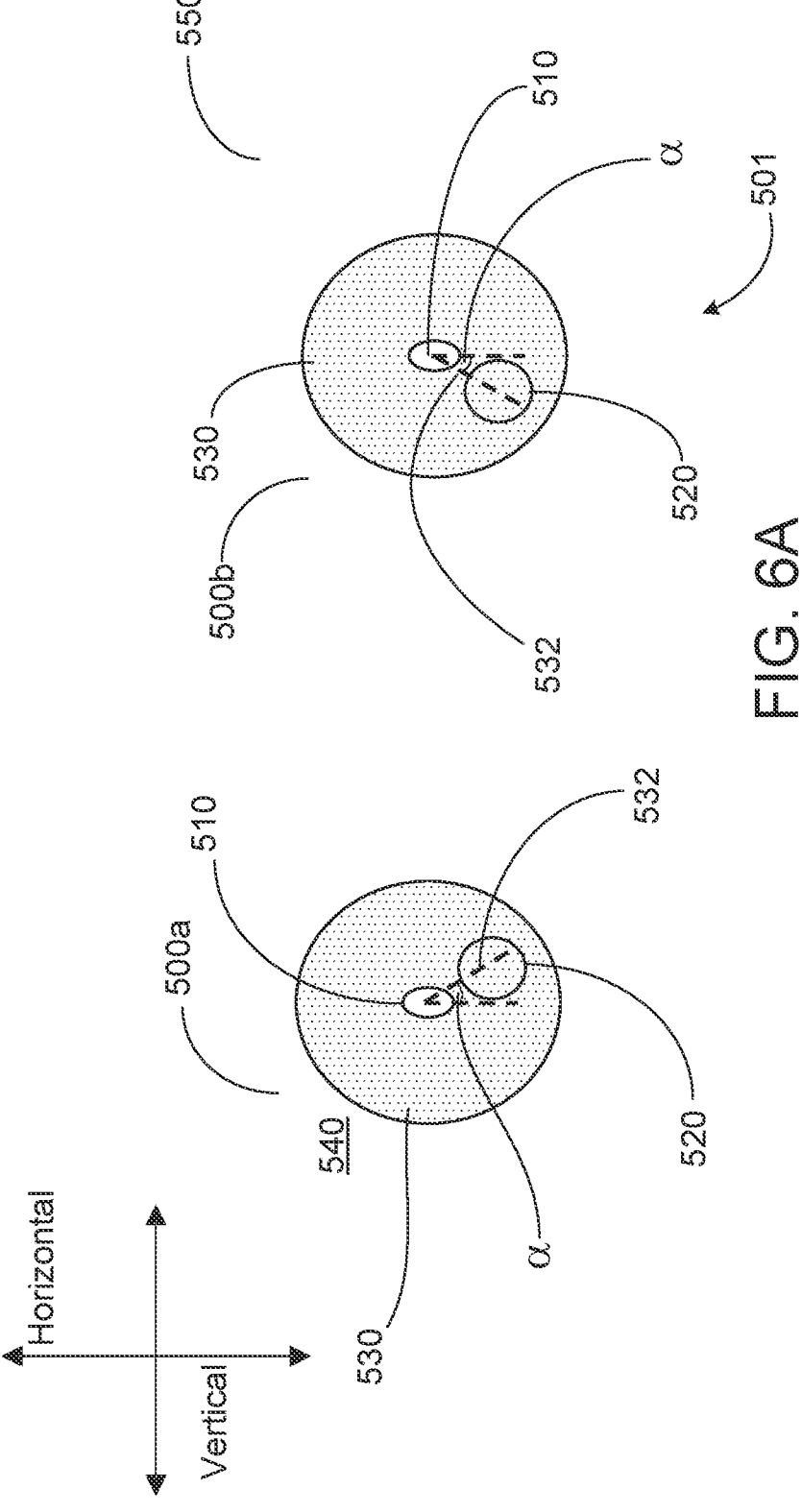
FIG. 6A shows a pair of spectacles containing ophthalmic lenses as shown in FIG. 5.

Referring to FIG. 6A, eyeglasses 501 include two lenses 500a and 500b in eyeglass frames 550. Each lens corresponds to lens 500 shown in FIG. 5, shaped and sized to fit frames 550 with the second clear aperture 520 aligned below clear aperture 510 along the axis 132, an angle α from the vertical axis. In each case, the offset angle α is in the direction of the user's nose. While this angle is the same in lenses 500a and 500b, in some embodiments, the offset angle can be different. For example, different offset angles can be used to accommodate variations between the vergence for each eye.

Figures 6B, 6C:
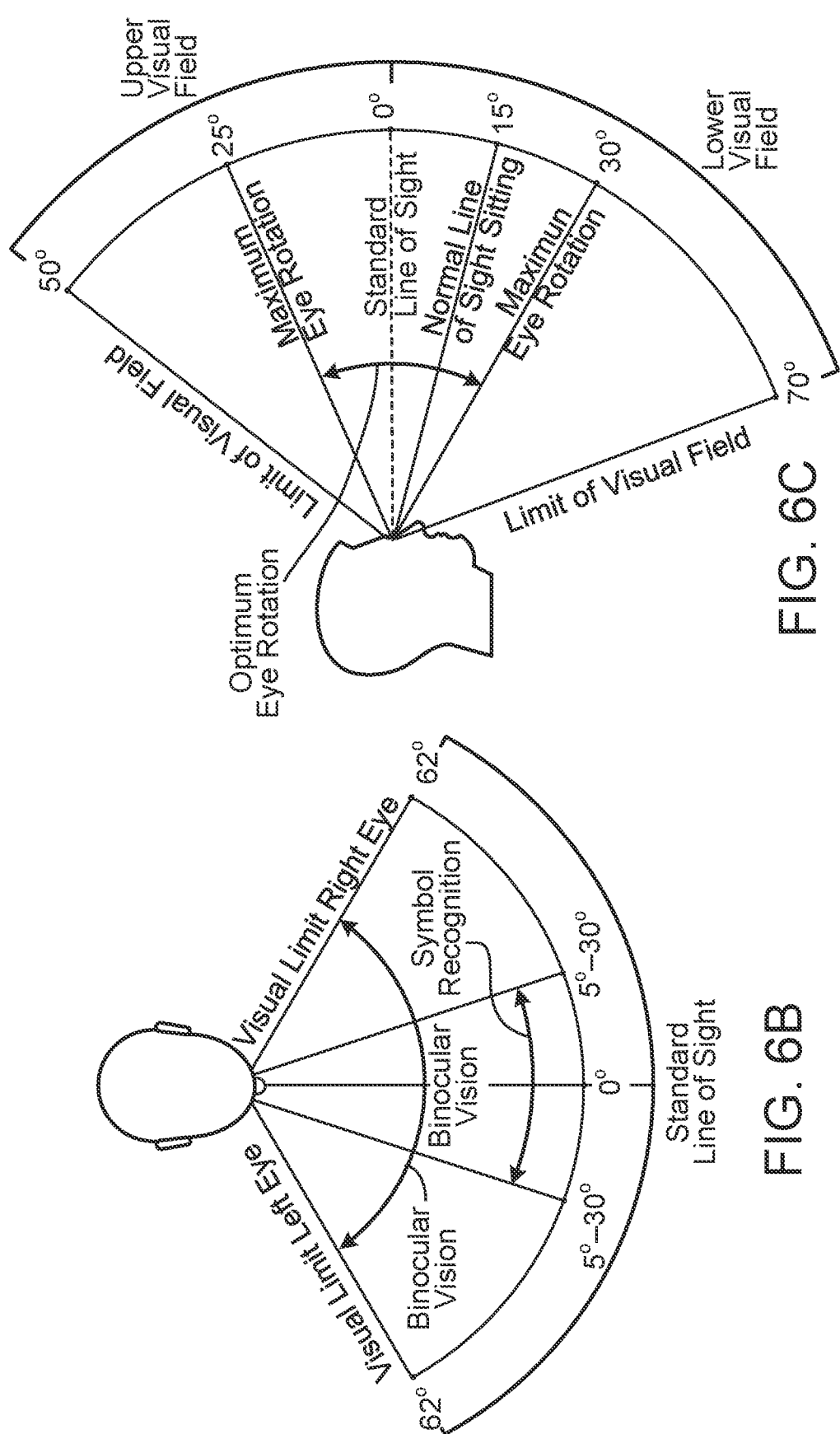
FIGS. 6B and 6C are diagrams illustrating horizontal and vertical fields of view, respectively, for a person.

Referring to FIGS. 6B and 6C, clear apertures 510 and 520 can be sized, shaped, and positioned in eyeglasses 501 to provide a line of sight through aperture 510 along the Standard Line of Sight of a user (e.g., for distance vision)

and to provide a line of sight through aperture 520 along the Normal Line of Sight Sitting (e.g., for near vision, such as for reading). Clear aperture 510 can be sized and positioned to provide a line of sight through the clear aperture for ±2° or more (e.g., ±3° or more, ±4° or more, ±5° or more, such as ±10° or less, ±9° or less, ±8° or less, ±7° or less, ±6° or less) in the vertical and/or horizontal directions. The angular range in the horizontal and vertical directions can be the same or different. The angular range in the upper visual field can be the same or different as the angular range in the lower visual field.

Clear aperture 520 can be sized and positioned to provide a line of sight through the clear aperture for ±2° or more (e.g., ±3° or more, ±4° or more, ±5° or more, such as ±10° or less, ±9° or less, ±8° or less, ±7° or less, ±6° or less) in the vertical and/or horizontal directions about the Normal Line of Sight Sitting axis. The angular range in the horizontal and vertical directions can be the same or different. In some embodiments, clear aperture 520 can have a horizontal width sufficient so that the user has a line of sight through the aperture in the Symbol Recognition region, e.g., at 15° below the Standard Line of Sight. For example, the horizontal width of clear aperture 120 can be sized to provide a line of sight through the clear aperture for up to ±30° (e.g., up to ±25°, up to ±20°, up to ±15°, up to ±12°).

While ophthalmic lens 500 features a circular distance vision aperture and a circular near vision aperture, more generally, one or both of these apertures can have non-circular shapes, e.g., to provide desired field of view side along the Standard Line of Sight axis and the Normal Line of Sight Sitting axis. For example, either or both clear apertures can be elliptical, polygonal, or have irregular shapes.

Additional patterns of optical elements for reducing myopia progression are shown in Appendix III, enclosed herewith.

As noted, the horizontal and vertical axes refer to how lens 500 is ultimately oriented in a pair of eyeglass frames. In an unmounted spectacle lens 500 prior to shaping the edge for mounting in a frame, where the lens is plano or spherical, such lenses are typically radially symmetric and the angle α is arbitrary until the lens is shaped for mounting. However, in lenses which do not possess radial symmetry, such as cylindrical powered or toric lenses, the angle α can alternatively be defined relative to the orientation of the second aperture 520 compared to the cylinder axis of the cylindrical component. In other words, in addition to aligning the aperture 510 to the appropriate point on the lens (e.g., the center of the lens), it is important to align the axis 532 relative to the cylinder axis of the lens.

Figures 7A, 7B, 7C, 7D:
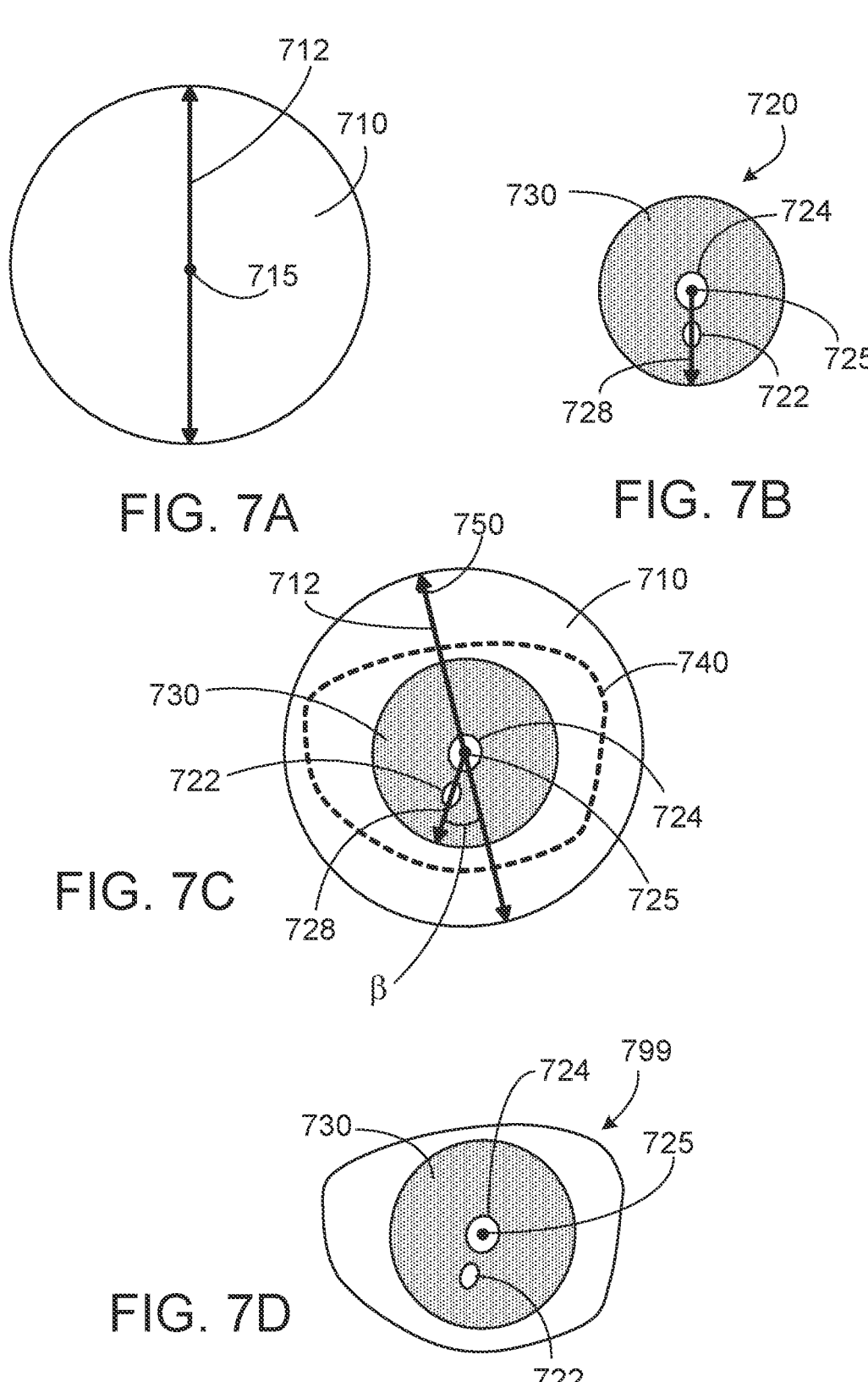
FIGS. 7A-7D illustrate steps in a process of manufacturing process an example ophthalmic lens featuring optical elements and a marker for specifying orientation of the lens.

This process is illustrated in FIGS. 7A-7D. Here, FIG. 7A shows a lens 710 having non-zero cylinder with cylinder axis 712. The geometric center 715 of lens 710 is also shown. FIG. 7B shows a pattern 720 of scattering centers. Pattern 720 includes a pair of apertures 722 and 724 arranged in an area 730 of scattering centers. An axis 728 running from the geometric center 725 of the pattern, which is also the geometric center of aperture 724, through the geometric center of aperture 722 is also shown.

FIG. 7C shows the relative alignment of pattern 720 with lens 710. In this example, the center 725 of pattern 720 is aligned with center 715 of lens 710. In addition to that, the pattern is aligned with axis 728 at an angle β with cylinder axis 712. The angle β can be specified, for example, based on the cyl axis of the user's prescription and the range of motion of their pupil from distance vision to near vision. FIG. 7C also shows the outline of the edge 740 of the lens once sized for a pair of eyeglass frames. A marker 750 is provided near the lens periphery, marking the cylinder axis providing a fiducial for aligning the lens and the pattern and for shaping the lens to its final form 799, shown in FIG. 7D. Marker 750 can be a printed or etched fiducial used to establish the orientation of the lens relative to the lens modification system before, during, or after forming pattern 720 on the lens and can be any optical feature identifiable by the alignment system used in conjunction with the lens modification system. The marker can be formed using the same system used for form pattern 720 or using a different system. In some embodiments, marker 750 is formed within the lens, in the bulk lens material.

While the foregoing example utilizes printed or etched fiducials, which are examples of optical features, to establish the orientation of the cylinder axis of the lens in order to form the pattern with the desired orientation, other features can be used for this purpose. For example, it is possible to measure the optical properties of the lens itself, i.e., to measure the cylinder axis and then use that measurement to properly align the pattern to the lens. Alternatively, or additionally, in some embodiments a physical feature can be used to establish the proper alignment of the lens.

Figures 8A, 8B, 8C, 8D:
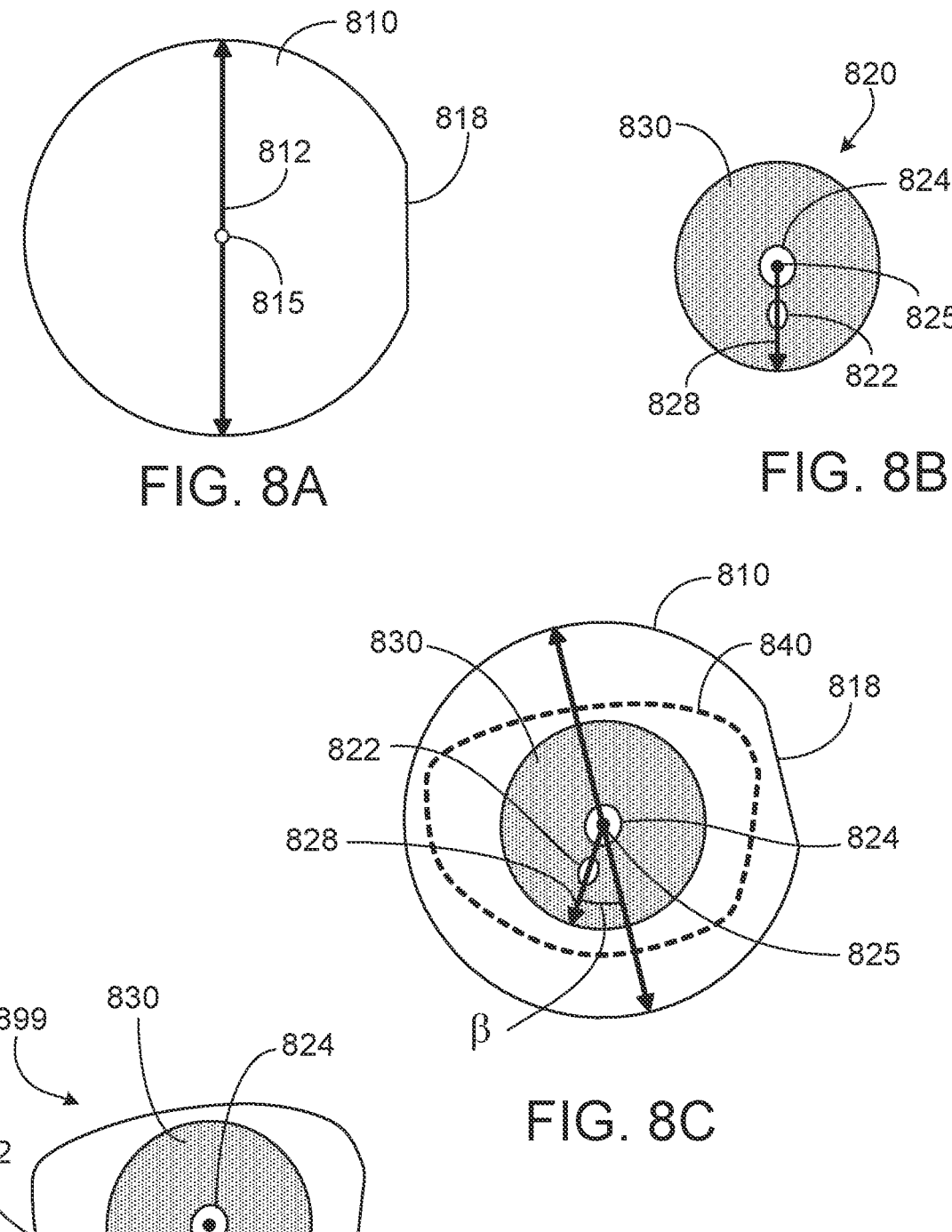
FIGS. 8A-8D illustrate steps in a process of manufacturing process an example ophthalmic lens featuring optical elements an edge feature for specifying orientation of the lens.

For example, referring to FIG. 8A, a lens 810 has non-zero cylinder with cylinder axis 812 and a straight-edged section 818 in the otherwise circular edge of the lens. The straight-edged section 818 is aligned parallel to axis 812. The geometric center 815 of lens 810 is also shown. Here, the geometric center of the lens refers to the center of the circle defined by the edge of lens 810.

FIG. 8B shows a pattern 820 of scattering centers for forming on lens 810. Pattern 820 includes a pair of apertures 822 and 824 arranged in an area 830 of scattering centers. An axis 828 running from the geometric center 825 of the pattern, which is also the geometric center of aperture 824, through the geometric center of aperture 822 is also shown.

FIG. 8C shows the relative alignment of pattern 820 with lens 810. In particular, the center 825 of pattern 820 is aligned with center 815 of lens 810. In addition to that, the pattern is aligned with axis 828 at an angle β with cylinder axis 812. FIG. 8C also shows the outline of the edge 740 of the lens once sized for a pair of eyeglass frames. Straight-edged section 818 is used to establish the vertical and horizontal directions for shaping the lens to its final form 899, shown in FIG. 8D.

Other types of physical features can be used for alignment purposes alternatively, or in addition to, edge 818. For example, in some embodiments, one or more notches can be made in the edge having a known relationship (e.g., aligned with or offset from by a known amount) with axis 812. The physical features can be formed on the lens before, during, or after forming the pattern on the lens.

Figures 9A, 9B, 9C:
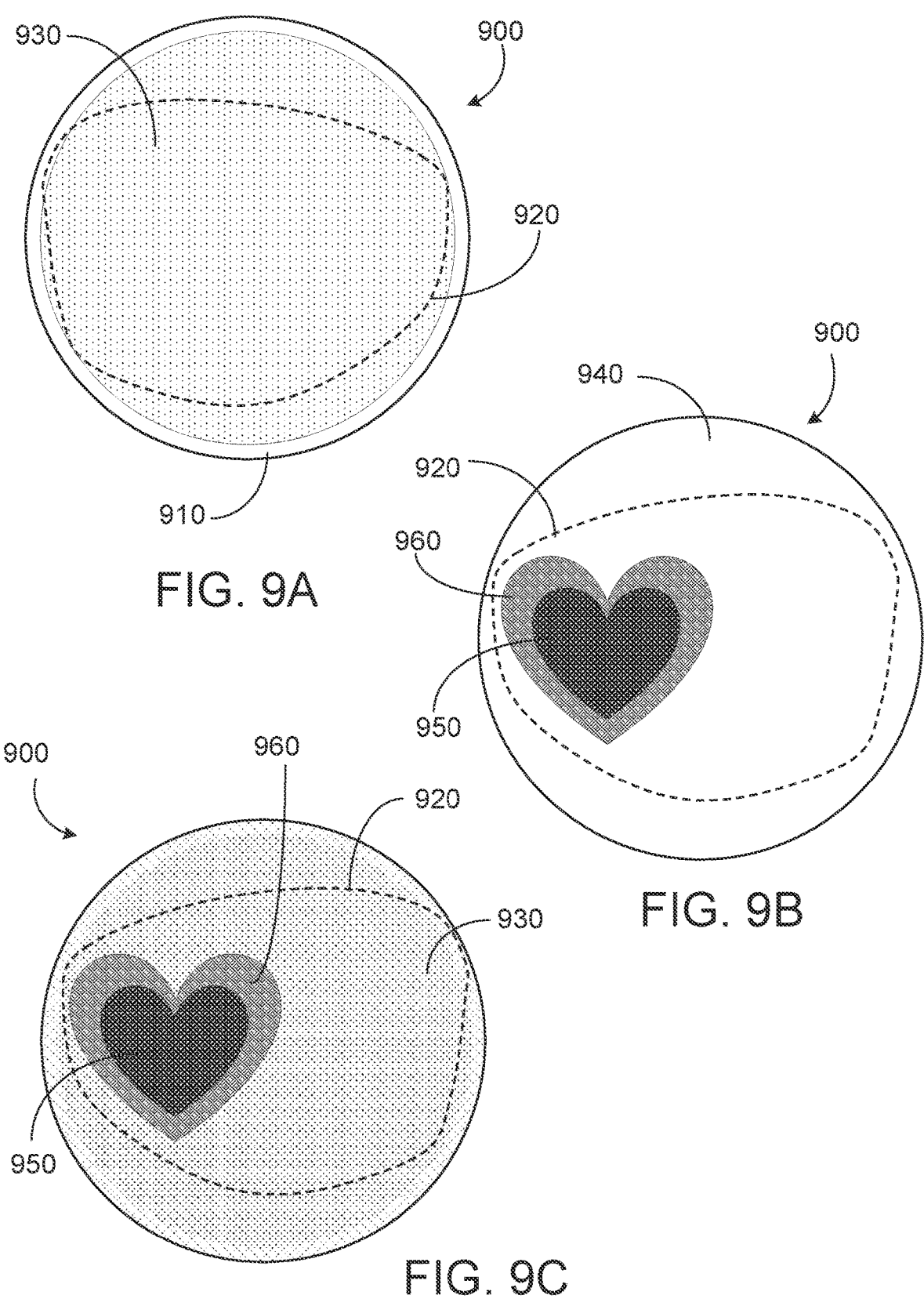
FIGS. 9A-9C illustrate steps in a process of manufacturing process an example ophthalmic lens featuring optical elements on both surfaces.

In the examples above, the pattern of optical elements occupies a geometric shape, such as a circle, and features optical elements arranged in a regular arrangement such as in an annular pattern, on a grid, or series of stripes, or in a random manner. However, as noted previously, irregular patterns or patterns having non-circular outlines (e.g., irregular outlines) can be used. Such patterns may be a recognizable shape or image. An example is shown in FIG. 9A. Here, a pattern 930 of optical elements in a circular area is formed on one side 910, e.g., the side facing the wearer, of a lens 900. An outline 920 of the lens shaped for eyeglass frames is shown.

On the opposite surface, a recognizable shape or images can be formed, such as an image, artwork, logo, and the like. The size or density of the pattern of optical elements can be varied so that parts of the pattern appear lighter or darker in reflection to an observer. The size or density of the optical patterns can be varied to create a grayscale image. If colored material is used for depositing or creating the optical elements, the size, density, and color of the optical patterns can be varied to create a color image. Similar to other rotationally asymmetric patterns, these patterns may have a specified orientation when mounted in eyeglass frames, or have a specified orientation on the eye when used as a contact lens. For example, as shown in FIG. 9B, side 940 of lens 900 features a heart-shaped pattern with an inner area of one density of optical elements and an outer area with a different density.

The resulting lens 900, shown in FIG. 9C, features optical elements on both side. The patterns on the front surface (i.e., facing away from the wearer during use) can be formed so that these shapes are visible to a person looking at the wearer without being perceptible to the wearer themselves.

The irregular shaped patterns shown in FIGS. 9A-9C are merely examples and more generally the techniques disclosed herein can be used to form patterns yielding much more complex imagery. In general, by varying the outline of the pattern, and the density and size of the optical elements, it is possible to provide eyeglasses that display almost any imagery that can be digitized. Accordingly, the disclosed techniques allow a user to customize their lenses to have names, signatures, logos, images of pets, family members, friends, pop culture figures and so on.

Moreover, by forming patterns on both sides the imagery can change depending on the relative location of the observer with respect to the lens due to the parallax effect of the two displaced images on the front side and the back side of the lens.

Figure 10:
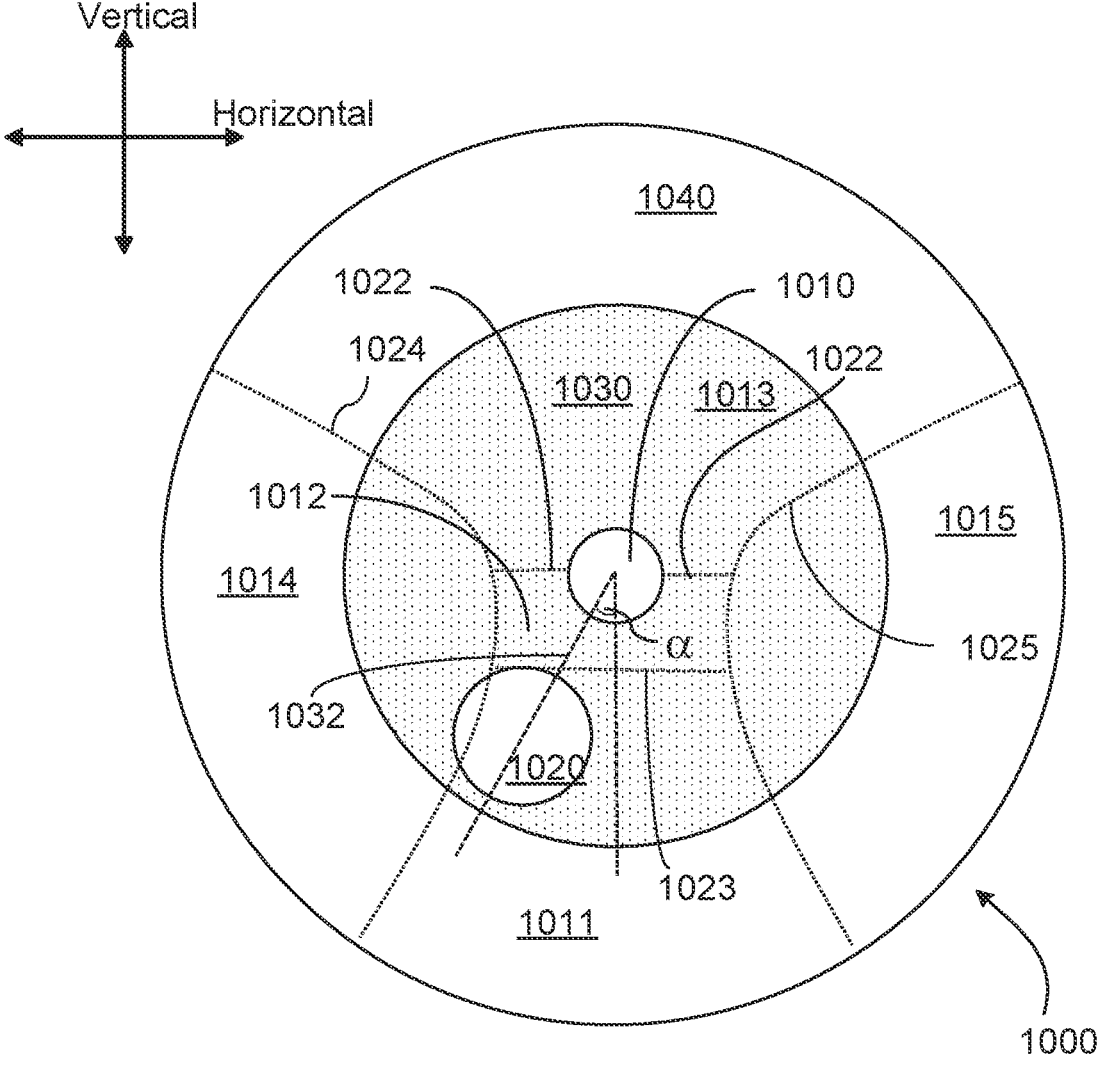
FIG. 10 is a plan view diagram of an example ophthalmic lens with a pattern of optical elements that includes two clear apertures.

The foregoing examples feature single vision lenses, such as plano, sphere, and toric lenses. More generally, multifocal lenses—such as progressive lenses or bifocal lenses—can also be used. Progressive lenses are radially asymmetric and typically characterized by a gradient of increasing lens power, added to the wearer's correction for the other refractive errors. The gradient starts at the wearer's distance prescription at the top of the lens and reaches a maximum addition power, or the full reading addition, lower in the lens to match the natural path of the eye as it focuses on near objects. The length of the progressive power gradient on the lens surface generally depends on the design of the lens, with a final addition power usually between 0.75 and 3.50 diopters. An example of a progressive lens with a rotationally asymmetric pattern is shown in FIG. 10.

As illustrated, lens 100O includes five different zones, separated by dotted lines 1022, 1023, 1024, and 1025 in the figure. These include a near-viewing zone 1011, an intermediate zone 1012, a distance-viewing zone 1013. Such a lens may also include peripheral distortion zones 1014 and 1015. Although demarcated by dotted lines, the variation in optical power from one zone to the next is typically gradual.

With respect to the scattering/clear properties of the lens, progressive ophthalmic lens 1000 includes a clear outer region 1040, a light scattering area 1030, and a first clear aperture 1010 for distance vision and a second clear aperture 1020 for near vision. Second clear aperture 1020 is aligned along an axis 1032 that is offset by an angle, a, from the vertical axis of the lens. Distance vision clear aperture 1010 overlaps (in this case, partially) with distance-viewing zone 1013 of the progressive lens, while near vision aperture 1020 overlaps with near-viewing zone 1011.

In some embodiments when a multifocal lens is used, the second clear aperture (e.g., aperture 1020 in lens 100O is aligned specifically on an area of the lens having add power for near vision. For example, the location of the second aperture can have an optical power of +0.25 D (e.g., +0.5 D or more, +0.75 D or more, +1.0 D or more, +1.25 D or more, +1.5 D or more, +1.75 D or more, +2.0 D or more) or more compared to the optical power of the lens at the first clear aperture (i.e., the aperture for distance vision).

As noted previously, other optical elements than scattering centers can be used as alternative, or in addition to, scattering centers. For example, a lens can include one or more lenslets having an optical power different from the base lens in the areas identified as "scattering areas" in the embodiments described above. More generally, the scattering area is also referred to as the patterned area. Examples of such lenslets are disclosed, for example, in U.S. Pat. No. 10,268,050 entitled "Spectacle Lens" issued on Apr. 23, 2019, in PCT Publication WO 2019/166653, entitled "Lens Element" published on Sep. 6, 2019, in PCT Publication WO 2019/166653, entitled "Lens Element" published on Sep. 6, 2019, PCT Publication WO 2019/166654, entitled "Lens Element" published on Sep. 6, 2019, PCT Publication WO 2019/166655, entitled "Lens Element" published on Sep. 6, 2019, PCT Publication WO 2019/166657, entitled "Lens Element" published on Sep. 6, 2019, PCT Publication WO 2019/166659, entitled "Lens Element" published on Sep. 6, 2019, and PCT Publication WO 2019/206569, entitled "Lens Element" published on Oct. 31, 2019. For example, lenslets for myopic defocus can be used. In some embodiments, the optical elements are annular refractive structures (e.g., Fresnel lenses) for myopic defocus, examples of which are shown in U.S. Pat. No. 7,506,983 entitled "Method of Optical Treatment" issued on Mar. 24, 2009.

Figure 11:
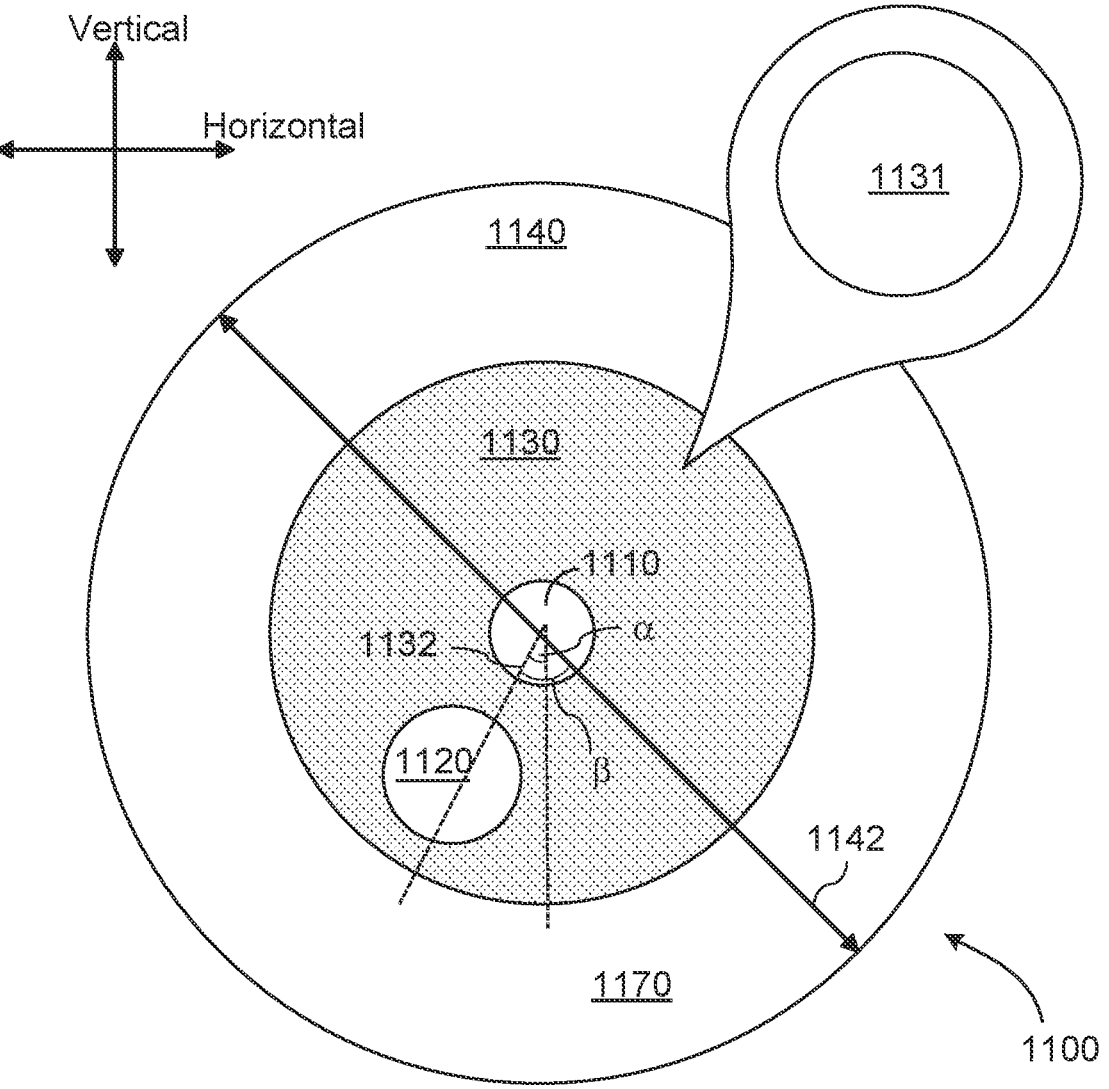
FIG. 11 is a plan view diagram of another example ophthalmic lens with a pattern of optical elements that includes two clear apertures.

An example of a rotationally asymmetric lens with a rotationally asymmetric pattern of lenslets is shown in FIG. 11. Here, a lens 1100 has a non-zero cylinder and a cylinder axis 1142. The pattern of optical elements includes a first clear aperture 1110 and an annular shaped area 1130 surrounding the clear aperture that features an array of lenslets 1131 (shown in inset) sized and shaped for myopic defocus. The lenslets introduce defocus to portions of a wavefront that would otherwise be focused onto the user's retina. First clear aperture 1110 is positioned substantially near the center of lens 1100. Myopic defocus area 1130 is also centered with respect to the lens center. Myopic defocus area 1130 is also surrounded by a clear area 1140. A second clear aperture 1120 is also provided in light scattering area 1130, separated from clear aperture 1110 along an axis 1132 that is offset by an angle $\alpha$ from the vertical axis of the lens. Cyl axis 1142 is aligned at an angle $\beta$ with respect to axis 1132.

Generally, the optical properties of lenslets can vary depending on the degree of defocus considered appropriate for a user. For example, the lenslets can be spherical or aspherical or contain higher order aberrations. The lenslets can have positive or negative optical power. In some embodiments, the optical power of the lenslets is zero (e.g., wherein the base power of the lens is strongly negative). The lenslets have each have the same optical power or different lenslets can have differing optical power. In some embodiments, lenslets can have an add power of +0.25 D or more (e.g., +0.5 D or more, +0.75 D or more, +1.0 D or more, +1.25 D or more, +1.5 D or more, +1.75 D or more, +2.0 D or more, +3.0 D or more, +4.0 D or more; such as up to +5.0 D) compared to the base optical power of the lens. In certain embodiments, lenslets can have an add power of −0.25 D or less (e.g., −0.5 D or less, −0.75 D or less, −1.0 D or less, −1.25 D or less, −1.5 D or less) compared to the base optical power of the lens.

The size of the lenslets can also vary as appropriate. The lenslets can have a diameter of 0.5 mm or more (e.g., 0.8 mm or more, 1 mm or more, 1.5 mm or more, 2 mm or more, 3 mm or more; such as up to 5 mm).

Figure 12:
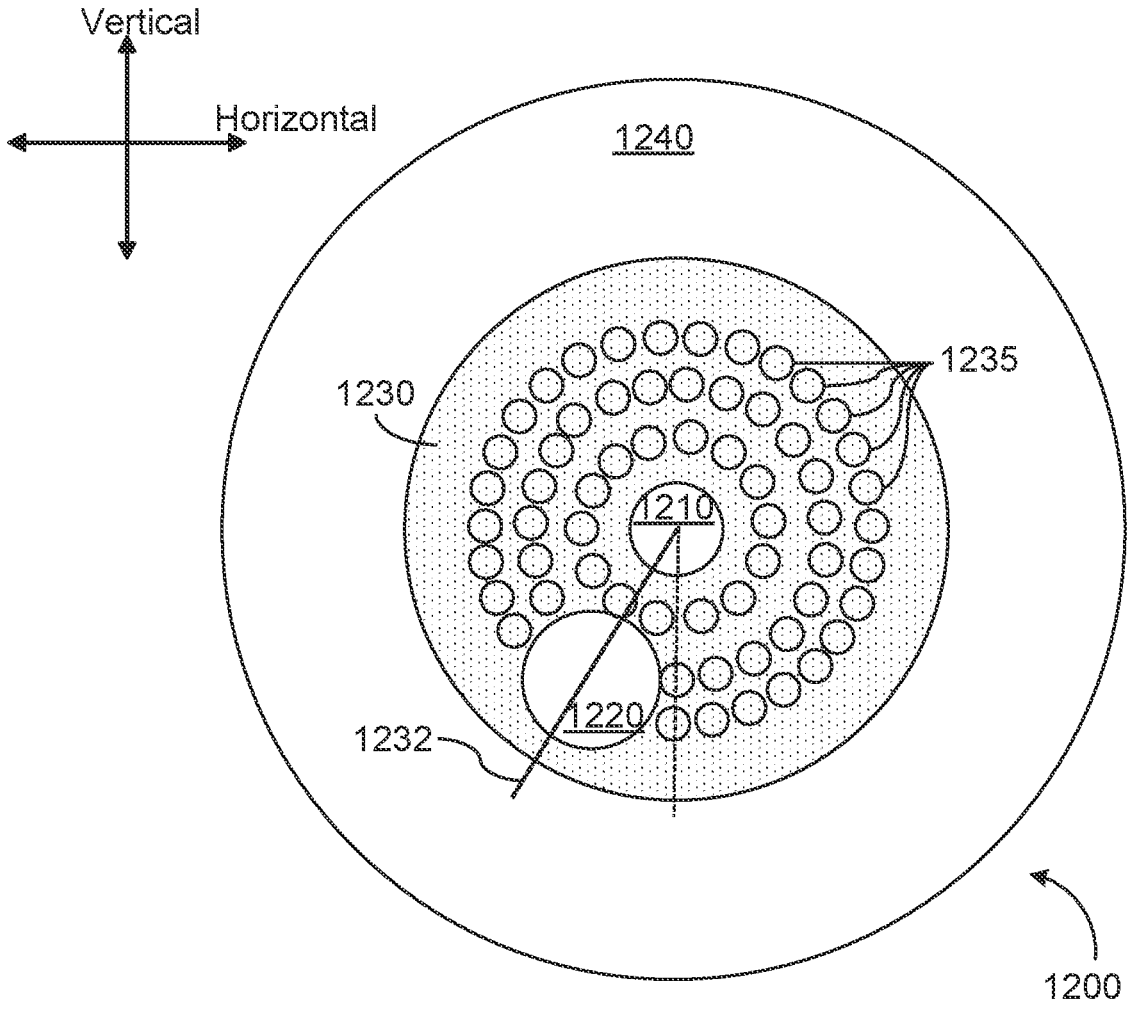
FIG. 12 is a plan view diagram of a further example ophthalmic lens with a pattern of optical elements that includes two clear apertures.

Some embodiments can include both lenslets and scattering centers. For example, referring to FIG. 12, an example lens 1200 includes a clear outer region 1240, a light scattering area 1230, a first clear aperture 1210 for distance vision and a second clear aperture 1220 for near vision. Second clear aperture 1220 is aligned along an axis 1232 that is offset by an angle, $\alpha$, from the vertical axis of the lens.

Scattering area 1230 includes scattering centers as described above. In addition, scattering area 1235 includes lenslets 1235 arranged in rings around aperture 1210. The lenslets introduce defocus to portions of a wavefront that would otherwise be focused onto the user's retina. Scattering centers are included at the locations of lenslets 1235. For example, scattering centers can be formed on a surface of each lenslet 1235, on the opposite lens surface but overlapping with the same lateral positions as lenslets 1235, and/or included within the bulk of lens 1200 overlapping laterally with lenslets 1235. In some embodiments, scattering centers are included between lenslets 1235, but do not laterally overlap with the lenslets. In certain embodiments, the scattering area of the lens includes only lenslets, but not additional scattering centers.

Figure 13:
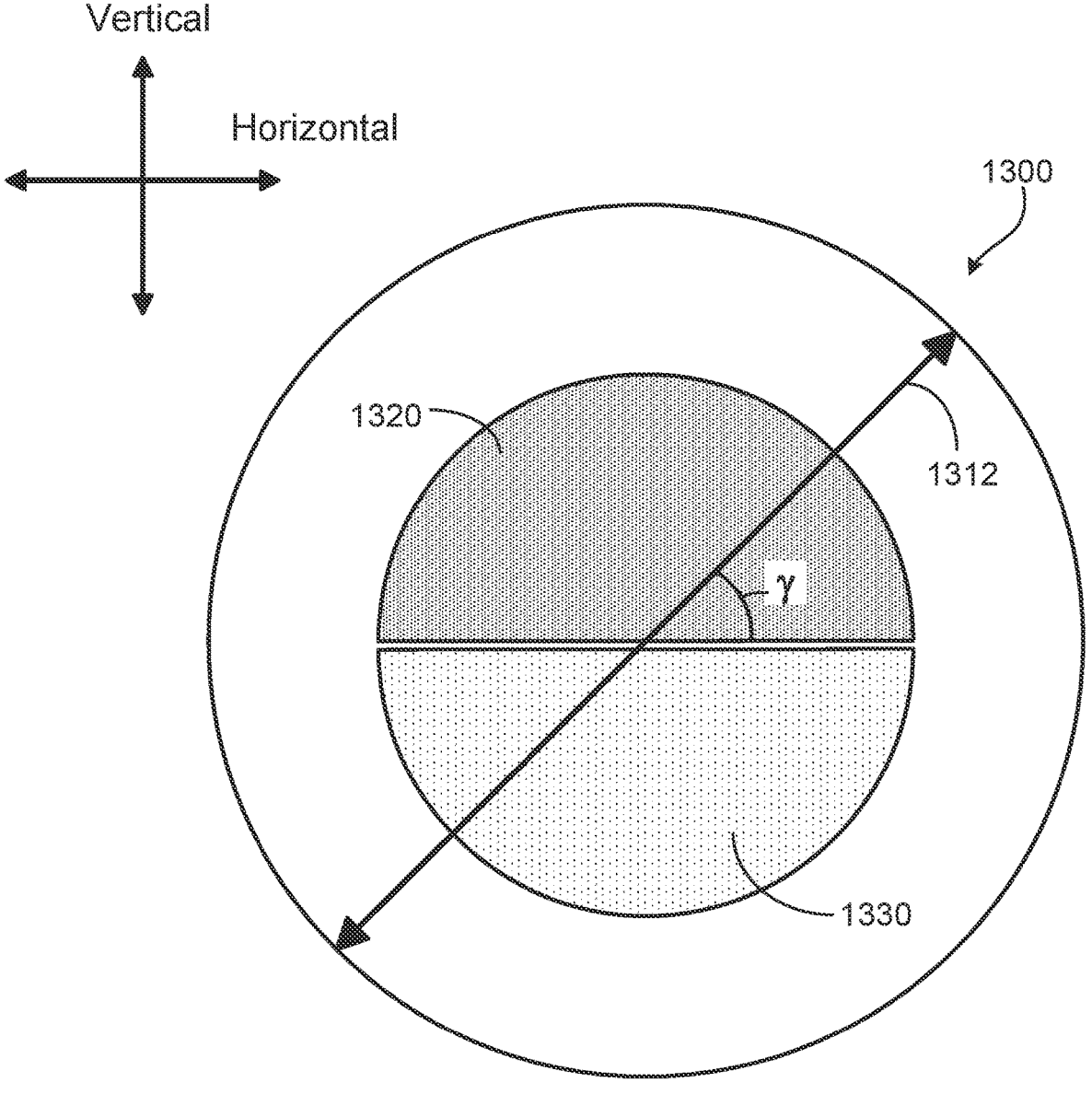
FIG. 13 is a plan view diagram of an example ophthalmic lens with a pattern of optical elements that includes no clear apertures.

A further example of a rotationally asymmetric lens with a rotationally asymmetric pattern is shown in FIG. 13, in which a lens 1300 having a cylinder axis 1312 at an angle $\gamma$ with respect to the horizontal direction. Lens 1300 includes a pattern of optical elements composed of two discrete zones: a top zone 1320 and a bottom zone 1330, each composing half the patterned area. The different zones 1320 and 1330 have different arrangements of optical elements. For example, depending on the implementation, the zones can have the same type of optical elements (e.g., scattering centers) but different densities. For instance, top zone 1330 can have a lower density of scattering centers than bottom zone 1320, providing increased scattering of light for light transmitted through the bottom zone. Alternatively, in certain embodiments, one zone can include lenslets and the other can feature scattering centers.

Other variations are also possible. For instance, more than two zones can be used and, in some embodiments, multiple zones can be used with one or more apertures.

FIGS. 10-13 each show an example of a lens that can be dispensed reliably and efficiently using a Just-in-Time process as described above. It will be understood that the disclosed techniques are more broadly applicable. For instance, while the foregoing examples relate to ophthalmic lenses for eyeglasses, the techniques can be applied to other types of ophthalmic lenses too, such as to contact lenses. In some embodiments, custom contact lenses that include patterns of optical elements can be delivered using the aforementioned techniques.

In some embodiments, the processes described herein can be incorporated into lens dispensing protocols that involve lens blocking for custom edging of the lens for specific eyeglass frames. For example, FIG. 15 is a flowchart showing steps in a method 1500 for customizing a standard finished single vision lens with a pattern of optical elements, edging the lens, and mounting it in a pair of eyeglass frames. Method 1500 incorporates several steps that are conventionally used to customize standard lenses for eyeglasses and can be integrated into established work flow with relatively little disruption.

In a first step 1510, a standard finished single vision lens is selected according to the Rx specified for the job, e.g., out of inventory. The lens can be a stock lens or a lens that has been resurfaced and/or coated as necessitated by the job.

The lens is inspected (1520) to ensure the lens power is as specified for the Rx, within tolerance. If the lens fails this inspection (1530), a new lens is selected and the inspection repeated. If the lens passes this inspection, then standard blocking is applied to the lens surface opposite from the surface to be patterned (1540), which is usually the convex front surface of the lens. Lens blocking refers to a process by which prescription lenses are prepared before their perimeter is cut to fit into wearable frames, the latter process is called edging. Typically, blocking involves detecting the optical center of the lens to ensure the lens is correctly shaped for mounting in the frames. Typically, blocking involves attaching (e.g., using an adhesive) a block (e.g., a disc-shaped object formed from, e.g., a plastic material, that protrudes from the lens surface) to a surface of the lens. The surfacing block can be mounted after identifying the optical center of the lens, or some other identifying characteristic of the lens, so that the block provides a reference location on the lens and a fiducial for the angular orientation of the lens. The block can also provide a physical extension of the lens by which the lens can be moved and/or reoriented relative to other processing equipment. Conventional blocking techniques can be used.

For the pattern forming process, the blocked lens is inserted into a jig (1550). This can be performed manually or robotically. Once mounted in the jig, the lens surface is presented to the laser engraver (1560). Alternatively, a robotic arm can hold the block and present the lens surface to the laser engraver. The laser engraving system determines the relative position of the lens surface to the laser beam and the pattern is engraved into the lens surface according to the pre-established pattern. The system engraves only those portions of the surface that lie within the edging boundary.

After engraving, the blocked lens is transferred to the edger (1570). This can be performed manually or robotically. The edger edges the lens according to the size and shape of the eyeglass frames that the lens is to be mounted in (1580).

After edging, the lens is unblocked and the lens cleaned (1590). Unblocking involves removing the surfacing block from the lens surface. Depending on how the block is adhered to the lens, this can be performed using a solvent, water blade, thermal treatment, and/or mechanically.

The clean, edged lens is then mounted in the eyeglass frames, and the eyeglasses inspected for defects prior to delivery to the user (1599).

Figure 14:
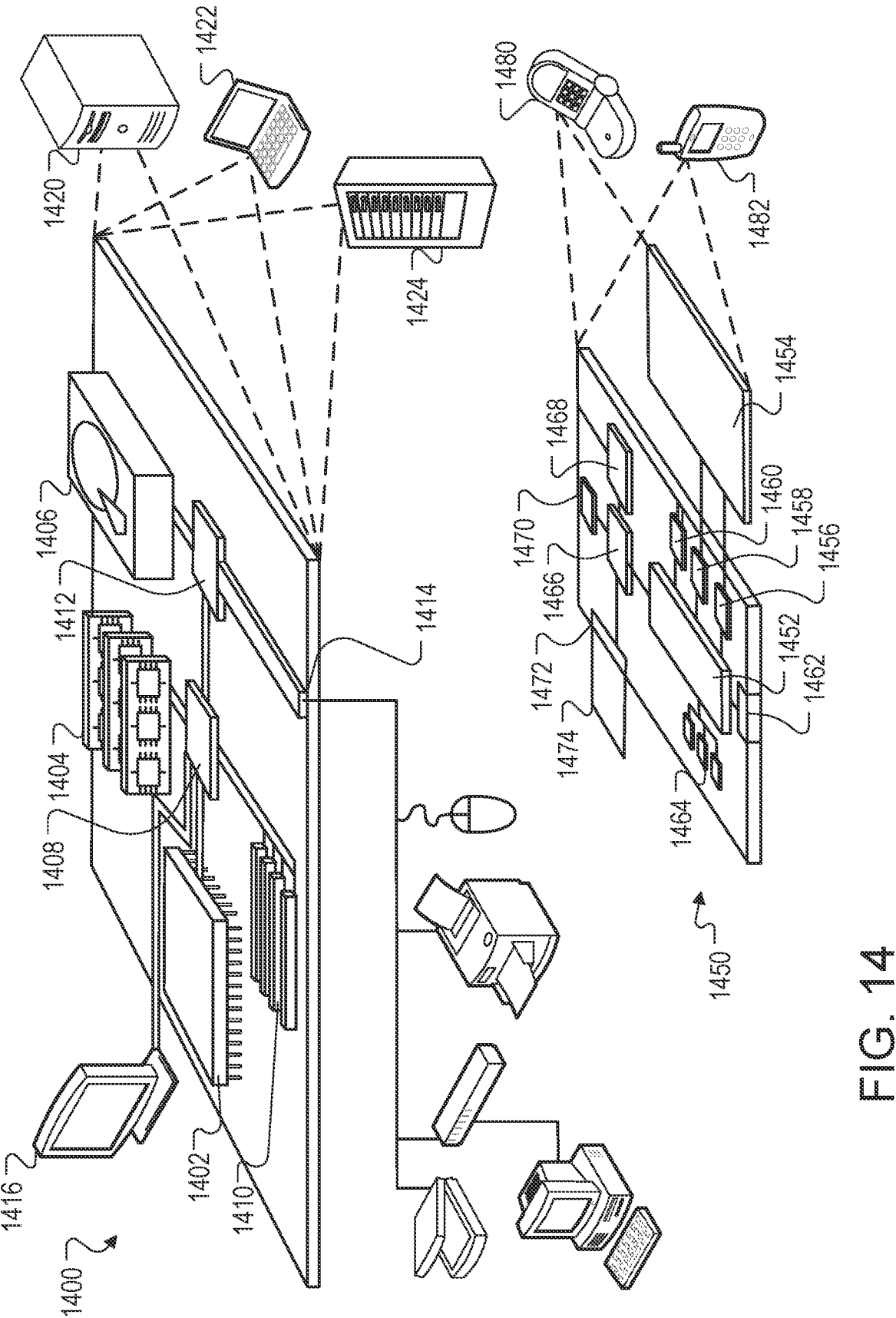
FIG. 14 is a schematic diagram illustrating data processing apparatus useable in a lens manufacturing system.

As noted previously, the systems and methods disclosed above utilize data processing apparatus to implement aspects of the Just-In-Time manufacturing described. FIG. 14 shows an example of a computing device 1400 and a mobile computing device 1450 that can be used as data processing apparatuses to implement the techniques described here. The computing device 1400 is intended to represent various forms of digital computers, such as laptops, desktops, workstations, personal digital assistants, servers, blade servers, mainframes, and other appropriate computers. The mobile computing device 1450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1404 stores information within the computing device 1400. In some implementations, the memory 1404 is a volatile memory unit or units. In some implementations, the memory 1404 is a non-volatile memory unit or units. The memory 1404 may also be another form of computer-readable medium, such as a magnetic or optical disk.

The storage device 1406 is capable of providing mass storage for the computing device 1400. In some implementations, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1402), perform one or more methods, such as those described above. The instructions can also be stored by one or more storage devices such as computer- or machine-readable mediums (for example, the memory 1404, the storage device 1406, or memory on the processor 1402).

The high-speed interface 1408 manages bandwidth-intensive operations for the computing device 1400, while the low-speed interface 1412 manages lower bandwidth-intensive operations. Such allocation of functions is an example only. In some implementations, the high-speed interface 1408 is coupled to the memory 1404, the display 1416 (e.g., through a graphics processor or accelerator), and to the high-speed expansion ports 1410, which may accept various expansion cards (not shown). In the implementation, the low-speed interface 1412 is coupled to the storage device 1406 and the low-speed expansion port 1414. The low-speed expansion port 1414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. In addition, it may be implemented in a personal computer such as a laptop computer 1422. It may also be implemented as part of a rack server system 1424. Alternatively, components from the computing device 1400 may be combined with other components in a mobile device (not shown), such as a mobile computing device 1450. Each of such devices may contain one or more of the computing device 1400 and the mobile computing device 1450, and an entire system may be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 may also be provided with a storage device, such as a micro-drive or other device, to provide additional storage. Each of the processor 1452, the memory 1464, the display 1454, the communication interface 1466, and the transceiver 1468, are interconnected using various buses, and several of the components may be mounted on a common motherboard or in other manners as appropriate.

The processor 1452 can execute instructions within the mobile computing device 1450, including instructions stored in the memory 1464. The processor 1452 may be implemented as a chipset of chips that include separate and multiple analog and digital processors. The processor 1452 may provide, for example, for coordination of the other components of the mobile computing device 1450, such as control of user interfaces, applications run by the mobile computing device 1450, and wireless communication by the mobile computing device 1450.

The processor 1452 may communicate with a user through a control interface 1458 and a display interface 1456 coupled to the display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may provide communication with the processor 1452, so as to enable near area communication of the mobile computing device 1450 with other devices. The external interface 1462 may provide, for example, for wired communication in some implementations, or for wireless communication in other implementations, and multiple interfaces may also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 may also be provided and connected to the mobile computing device 1450 through an expansion interface 1472, which may include, for example, a SIMM (Single In Line Memory Module) card interface. The expansion memory 1474 may provide extra storage space for the mobile computing device 1450, or may also store applications or other information for the mobile computing device 1450. Specifically, the expansion memory 1474 may include instructions to carry out or supplement the processes described above, and may include secure information also. Thus, for example, the expansion memory 1474 may be provide as a security module for the mobile computing device 1450, and may be programmed with instructions that permit secure use of the mobile computing device 1450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 1452), perform one or more methods, such as those described above. The instructions can also be stored by one or more storage devices, such as one or more computer- or machine-readable mediums (for example, the memory 1464, the expansion memory 1474, or memory on the processor 1452). In some implementations, the instructions can be received in a propagated signal, for example, over the transceiver 768 or the external interface 1462.

The mobile computing device 1450 may communicate wirelessly through the communication interface 1466, which may include digital signal processing circuitry where necessary. The communication interface 1466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1468 using a radio-frequency. In addition, short-range communication may occur, such as using a Bluetooth, WiFi, or other such transceiver (not shown). In addition, a GPS (Global Positioning System) receiver module 1470 may provide additional navigation- and location-related wireless data to the mobile computing device 1450, which may be used as appropriate by applications running on the mobile computing device 1450.

The mobile computing device 1450 may also communicate audibly using an audio codec 1460, which may receive spoken information from a user and convert it to usable digital information. The audio codec 1460 may likewise generate audible sound for a user, such as through a speaker, e.g., in a handset of the mobile computing device 1450. Such sound may include sound from voice telephone calls, may include recorded sound (e.g., voice messages, music files, etc.) and may also include sound generated by applications operating on the mobile computing device 1450.

The mobile computing device 1450 may be implemented in a number of different forms, as shown in the figure. For example, it may be implemented as a cellular telephone 1480. It may also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some embodiments, the computing system can be cloud based and/or centrally calculating the pattern. In such case anonymous input and output data can be stored for further analysis. In a cloud based and/or calculation center set-up, compared to distributed calculation of the patterns, it is easier to ensure data quality, and accomplish maintenance and updates to the calculation engine, compliance to data privacy regulations and troubleshooting.

Although a few implementations have been described in detail above, other modifications are possible. For example, while a client application is described as accessing the delegate(s), in other implementations the delegate(s) may be employed by other applications implemented by one or more processors, such as an application executing on one or more servers. In addition, the logic flows depicted in the figures do not require the particular order shown, or sequential order, to achieve desirable results. In addition, other actions may be provided, or actions may be eliminated, from the described flows, and other components may be added to, or removed from, the described systems.

A number of embodiments have been described, other embodiments are in the following claims.

What is claimed is:

1. A method, comprising:

providing an ophthalmic lens having opposing surfaces defining a prescription (Rx) optical power of the ophthalmic lens, the opposing surfaces further defining an optical center of the ophthalmic lens, and the ophthalmic lens comprising an edge defining a perimeter of the ophthalmic lens;

obtaining a pattern of three or more optical elements;

rotating the pattern about an optical axis of the ophthalmic lens; and after rotating the pattern, forming the optical elements on the lens according to the pattern, wherein the three or more optical elements each have an optical effect different from the Rx optical power of the ophthalmic lens, and after forming the optical elements the Rx optical power of the ophthalmic lens remains unchanged, wherein (i) the pattern is radially asymmetric, or (ii) the ophthalmic lens has at least one optical or structural characteristic that is radially asymmetric with respect to the ophthalmic lens; and wherein (i) the ophthalmic lens is radially asymmetric and the pattern is formed on the ophthalmic lens according to a specified orientation, or (ii) one or more optical or structural features are formed within the ophthalmic lens, on at least one surface of the ophthalmic lens, and/or at edge of the ophthalmic lens, the one or more optical or structural features specifying a rotational orientation of the ophthalmic lens.

2. The method of claim 1, wherein the pattern is selected to reduce progression of myopia in a human patient.

3. The method of claim 1, wherein the optical elements are selected from the group consisting of protrusions on one or both of the surfaces, depressions on one or both of the surfaces, and inclusions in a material of the ophthalmic lens having a refractive index different from a refractive index of the material of the ophthalmic lens.

4. The method of claim 1, wherein the optical elements are selected from the group consisting of light scattering centers, lenslets, and annular Fresnel lens elements.

5. The method of claim 1, wherein the optical elements comprise light scattering centers which reduce a contrast of an image viewer by a user of the ophthalmic lens viewed through the pattern.

6. The method of claim 1, wherein the optical elements comprise one or more lenslets having an optical power different from the optical power of the ophthalmic lens that provide myopic defocus for a human patient.

7. The method of claim 1, wherein the pattern comprises one or more apertures free of the optical elements.

8. The method of claim 7, wherein the optical axis of the lens intersects an aperture of the one or more apertures.

9. The method of claim 1, wherein an outline of the pattern and/or a density distribution of the optical elements define an image viewable from a world side of eyeglasses containing the ophthalmic lens.

10. The method of claim 1, wherein the pattern is obtained by determining the pattern based on one or more input parameter values selected from the group consisting of: a lens prescription for a human patient, a pupil size of the human patient, a vergence of the human patient, a pupillary distance of the human patient, a gaze angle of the human patient, a measure of myopic progression of the human patient, a predisposition of the human patient to myopia, a measure of conspicuity of the pattern of optical elements, a measure of comfort level of the human patient, an optical center height for a given pupil relative to a spectacle frame, the lens final shape and size once mounted to the spectacle frame, a user preference, and an eyecare professional's preference.

11. The method of claim 1, wherein the pattern is obtained by selecting the pattern from among a plurality of predetermined patterns, wherein the pattern specifies a size, shape, and relative location of the three or more optical elements.

12. The method of claim 1, wherein the optical elements are formed on one or both of the opposing surfaces of the ophthalmic lens or in a lens material of the ophthalmic lens.

13. The method of claim 1, wherein the ophthalmic lens is an eyeglass lens or a contact lens.

14. The method of claim 1, wherein the pattern is obtained based on at least one parameter associated with a human patient.

15. The method of claim 1, wherein the at least one optical or structural characteristic comprises a shape of the perimeter of the ophthalmic lens.

16. The method of claim 15, wherein the perimeter of the ophthalmic lens is shaped to fit a spectacle frame.

17. The method of claim 15, wherein the perimeter of the ophthalmic lens defines a circle and the at least one optical or structural characteristic comprises a deviation of the edge of the lens from the circle.

18. The method of claim 15, wherein the at least one optical or structural characteristic comprises one or more fiducial markings on one of the surfaces and/or the edge of the ophthalmic lens.

19. The method of claim 1, wherein the ophthalmic lens is for correcting an astigmatism and the at least one structural characteristic comprises a cylinder axis of the ophthalmic lens.

20. The method of claim 1, wherein the ophthalmic lens is a multifocal lens and the at least one structural characteristic comprises an optical power distribution of the multifocal lens.

21. The method of claim 1, further comprising:

measuring the optical axis of the ophthalmic lens; and determining where to form the optical elements on the surface of the ophthalmic lens based on the measurement of the optical axis.

22. The method of claim 1, wherein forming the optical elements comprises selectively exposing the surface of the ophthalmic lens to laser radiation.

23. The method of claim 22, wherein the laser radiation has a wavelength and a power sufficient to selectively melt, foam, or ablate a lens material of the ophthalmic lens at a surface of the ophthalmic lens.

24. The method of claim 1, wherein forming the optical elements comprises selectively depositing a material onto the surface of the ophthalmic lens.

25. The method of claim 1, further comprising shaping the edge of the ophthalmic lens according to a pair of eyeglass frames.

* * * * *